(12) United States Patent
Zhou

(10) Patent No.: US 11,457,723 B2
(45) Date of Patent: Oct. 4, 2022

(54) ORAL CLEANING KIT

(71) Applicant: Xing Zhou, Guangzhou (CN)

(72) Inventor: Xing Zhou, Guangzhou (CN)

( * ) Notice: Subject to any disclaimer, the term of this patent is extended or adjusted under 35 U.S.C. 154(b) by 627 days.

(21) Appl. No.: 16/212,467

(22) Filed: Dec. 6, 2018

(65) Prior Publication Data

US 2019/0104836 A1 Apr. 11, 2019

Related U.S. Application Data

(63) Continuation of application No. PCT/CN2017/086827, filed on Jun. 1, 2017.

(30) Foreign Application Priority Data

May 28, 2017 (CN) .......................... 201710394117.6

(51) Int. Cl.
*A47K 5/18* (2006.01)
*A46B 15/00* (2006.01)
(Continued)

(52) U.S. Cl.
CPC ...... *A46B 15/0002* (2013.01); *A46B 15/0091* (2013.01); *A47K 5/18* (2013.01);
(Continued)

(58) Field of Classification Search
CPC .......... A46B 15/0091; A46B 2200/108; A46B 2200/1066; A47K 5/18; A61Q 11/00;
(Continued)

(56) References Cited

U.S. PATENT DOCUMENTS

| 390,089 | A | * | 9/1888 | McClelland |
| 1,509,894 | A | * | 9/1924 | Axness ................. A45D 44/18 |
| | | | | 132/308 |

(Continued)

FOREIGN PATENT DOCUMENTS

| CN | 201055082 Y | 5/2008 |
| CN | 201223465 Y | 4/2009 |

(Continued)

OTHER PUBLICATIONS

International Search Report and Written Opinion, PCT/CN2017/086827, dated Feb. 11, 2018, 13 pgs.

(Continued)

*Primary Examiner* — Cris L. Rodriguez
*Assistant Examiner* — Brianne E Kalach
(74) *Attorney, Agent, or Firm* — Morgan, Lewis & Bockius LLP

(57) ABSTRACT

Disclosed is an oral cleaning kit, including an interdental brush, an oral viewer, a container, and a holder. The container includes an upper cover and a base. Oral cleaning appliances such as the interdental brush, the oral viewer, toothpaste and a toothbrush may be disposed in the container. The base includes a fixed clamping ring and a storage tank. The upper cover may be used as a tooth mug and is detachably mounted on the base. The holder may be provided on the container. When the holder is unfolded, a mobile phone may be disposed on the holder, and the cleaning process may be observed through the mobile phone in real time. The oral cleaning kit has the advantages of carrying convenience, simple use and hygiene.

19 Claims, 30 Drawing Sheets

(51) Int. Cl.
  *A61C 15/04* (2006.01)
  *A61B 1/247* (2006.01)
  *A61C 17/34* (2006.01)
  *A61B 1/06* (2006.01)
  *A61C 17/22* (2006.01)
  *A46B 9/04* (2006.01)
  *A46B 11/00* (2006.01)
  *A61C 19/02* (2006.01)

(52) U.S. Cl.
  CPC ............... *A61B 1/06* (2013.01); *A61B 1/247* (2013.01); *A61C 15/04* (2013.01); *A61C 15/047* (2013.01); *A61C 17/222* (2013.01); *A61C 17/34* (2013.01); *A46B 9/04* (2013.01); *A46B 11/0065* (2013.01); *A46B 2200/108* (2013.01); *A46B 2200/1066* (2013.01); *A61C 19/02* (2013.01)

(58) Field of Classification Search
  CPC ..... A61C 15/043; A61C 19/02; A61C 17/224; A45D 44/18; A45D 27/22; A45D 42/00; A45D 42/02; A45D 42/08; A45D 42/16
  USPC ............................. 206/760, 45.26, 749, 581
  See application file for complete search history.

(56) References Cited

U.S. PATENT DOCUMENTS

| | | | | |
|---|---|---|---|---|
| 1,975,691 A * | 10/1934 | Hibbs | | A47K 1/09 211/65 |
| 1,990,439 A * | 2/1935 | Murphy | | A45D 27/28 132/314 |
| 2,556,584 A * | 6/1951 | Frank | | B65D 35/56 132/308 |
| 2,593,896 A * | 4/1952 | Kollontay | | A45C 11/008 132/314 |
| 2,611,380 A * | 9/1952 | Grower | | A45D 27/22 132/289 |
| 2,965,109 A * | 12/1960 | Borah | | A45D 44/18 132/289 |
| 3,463,994 A * | 8/1969 | Spohr | | H01H 13/08 320/115 |
| 3,734,106 A * | 5/1973 | Zimmerman | | A46B 5/0095 132/311 |
| D231,593 S * | 5/1974 | Ockerman | | D6/531 |
| 4,768,530 A * | 9/1988 | Vaughn | | A45D 27/22 132/289 |
| 4,979,525 A * | 12/1990 | Chiou | | A45D 27/22 132/286 |
| 5,095,924 A * | 3/1992 | Stanfield | | A45D 44/18 132/310 |
| 5,163,561 A * | 11/1992 | Fitzgerald | | A46B 5/0095 15/145 |
| 5,215,193 A * | 6/1993 | Dennis | | A47K 5/18 132/309 |
| 5,344,015 A * | 9/1994 | Carlin | | A47G 1/12 206/425 |
| 5,653,343 A * | 8/1997 | Imai | | A45D 44/18 132/311 |
| D408,987 S * | 5/1999 | Balash | | D3/205 |
| 6,186,324 B1 * | 2/2001 | Catterson | | A45D 44/18 206/15.2 |
| 6,220,253 B1 * | 4/2001 | Wright | | A45C 11/008 132/310 |
| D457,718 S * | 5/2002 | McDonald | | D3/205 |
| 6,386,211 B1 * | 5/2002 | Smith | | A45D 44/18 132/286 |
| 6,681,780 B1 * | 1/2004 | Baxter | | A45D 33/008 132/295 |
| 6,895,976 B2 * | 5/2005 | Hetzler | | A45D 44/18 132/308 |
| D524,929 S * | 7/2006 | Young | | D23/377 |
| 10,362,697 B2 * | 7/2019 | Yuan | | H05K 5/0234 |
| 2003/0034459 A1 * | 2/2003 | Bonin | | A61L 2/06 250/491.1 |
| 2005/0252793 A1 | 11/2005 | Wilkinson | | |
| 2006/0027246 A1 * | 2/2006 | Wilkinson | | A45D 44/18 132/309 |
| 2008/0179323 A1 * | 7/2008 | Circosta | | A45D 44/18 220/8 |
| 2009/0148808 A1 * | 6/2009 | Alexander | | A61N 5/0603 433/29 |
| 2011/0297566 A1 * | 12/2011 | Gallagher | | F16M 11/105 206/320 |
| 2016/0317268 A1 * | 11/2016 | Dietzel | | A46B 17/065 |
| 2017/0340421 A1 * | 11/2017 | Eidenbenz | | A46B 7/023 |

FOREIGN PATENT DOCUMENTS

| | | |
|---|---|---|
| CN | 101861108 A | 10/2010 |
| CN | 202739860 U | 2/2013 |
| CN | 102972968 A | 3/2013 |
| CN | 104921826 A | 9/2015 |
| CN | 205053948 U | 3/2016 |
| CN | 205082842 U | 3/2016 |
| CN | 205545764 U | 8/2016 |
| CN | 205829924 U | 12/2016 |
| CN | 205947879 U | 2/2017 |
| CN | 206102289 U | 4/2017 |
| DE | 202005015201 U1 | 12/2005 |
| GB | 2127680 * | 8/1983 |
| KR | 100709560 B1 | 4/2007 |
| WO | WO98/01054 A1 | 1/1998 |
| WO | WO2010060166 A3 | 2/2012 |
| WO | WO2012121720 A1 | 9/2012 |
| WO | WO2014/069805 A1 | 5/2014 |
| WO | WO2015/135459 A1 | 9/2015 |
| WO | WO2016035961 A1 | 3/2016 |

OTHER PUBLICATIONS

Zhou, Xing, Extended European Search Report, EP17912174.4, dated Feb. 24, 2021, 8 pgs.

* cited by examiner

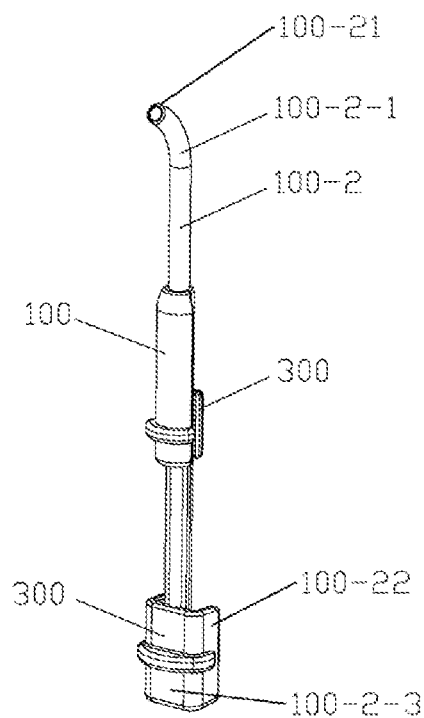
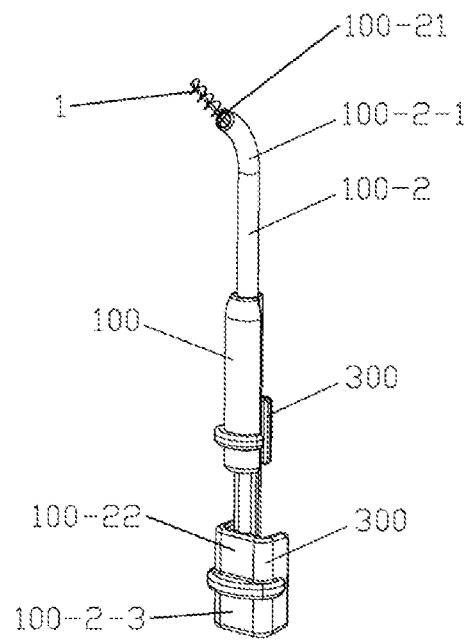
FIG. 6     FIG. 6-1
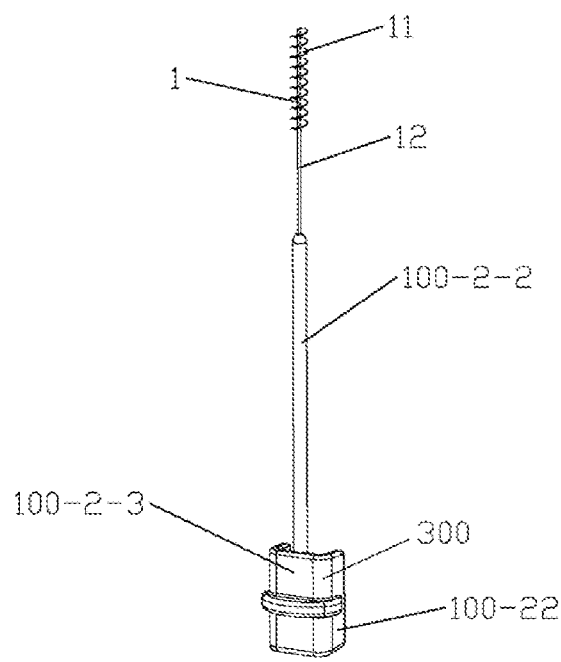
FIG. 7

ORAL CLEANING KIT

CROSS-REFERENCE TO RELATED APPLICATIONS

The application is a continuation application of PCT/CN2017/086827, entitled "ORAL CLEANING KIT" filed on Jun. 1, 2017, which claims priority to Chinese Patent Application No. 201710394117.6, filed with the State Intellectual Property Office of the People's Republic of China on May 28, 2017, and entitled "ORAL CLEANING KIT", all of which are hereby incorporated by reference in their entirety.

TECHNICAL FIELD

The present disclosure relates to an oral cleaning kit, and more particularly to an oral cleaning kit for cleaning tooth gaps and observing an oral cavity.

BACKGROUND

Oral cleaning is daily care that everyone must perform every day, especially with age, or pathological reasons, it is very easy to cause gingival recession and enlargement of tooth gaps, and it is very prone to food residue. If an oral cavity cannot be cleaned in time, on the one hand, bad breath may be produced, and on the other hand, various dental diseases, oral diseases, and especially periodontitis may occur.

In view of this situation, various interdental brushes, also known as interdental brushes, have been developed on the current market for users to choose. Although there are products of various structures and different specifications on the market today, the existing products are generally disadvantageous in that it is unlikely to observe tooth gaps. Especially when cleaning a gap between the third molar and the second molar or a gap between the second molar and the first molar or a gap between the first molar and the second premolar. Because the position of a tooth gap to be cleaned is deep in the mouth, the light is very dark in the cleaned part. When there is no external lighting, a user can operate only by feeling. The working part of an interdental brush in the prior art usually adopts a brush structure of attaching polymer material fibers to a metal wire. Therefore, when operating by feeling, the metal wire is very easy to stab gingival tissues and cause bleeding or damage to the gums.

In order to prevent the metal wire from stabbing the gums, the interdental brush in the prior art also includes an interdental brush made of a soft polymer material. Although the head of the interdental brush becomes soft and reduces the stab on the gums, it is prone to bending deformation due to low strength of the interdental brush. Therefore, the interdental brush slightly misaligns to the tooth gap, it is difficult to push bristles of the interdental brush into the tooth gap, and it is difficult to successfully clean the tooth gap. Therefore, when using this interdental brush, the visibility of the use process is more demanding.

Based on the above-mentioned technical shortcomings, the applicant applied for Chinese Patent No. 201410091268.0, filed on Mar. 12, 2014 and entitled "Internal Interdental Brush"; the applicant applied for Chinese Patent No. 201410108525.7, filed on Mar. 21, 2014 and entitled "Visual Interdental Brush"; and the applicant filed a PCT application for the above patents, and the PCT patent application number is PCT/CN2015/073927. The above patents have all technically improved the technical shortcomings of the foregoing interdental brush.

Meanwhile, the applicant has also found that for most users, daily oral cleaning needs to be performed in time after eating, and in a complete oral cleaning process, a variety of tools are needed: observation tools such as an oral viewer; cleaning tools such as an interdental brush, a toothbrush, toothpaste, and dental floss. When oral cleaning is performed during business hours or travel time, dental cleaning is usually performed in public toilets. Therefore, it is necessary to further improve the problems how to realize the carrying-out of tools such as an interdental brush, an oral viewer and a toothbrush, as well as the use convenience and hygiene in public toilets.

SUMMARY

The present disclosure is directed to a portable oral cleaning kit that is hygienic and convenient to use in various toilets.

The present disclosure provides an oral cleaning kit. The oral cleaning kit 800 is characterized by including an interdental brush 1, an oral viewer 2, and a container 3 capable of containing the interdental brush 1 and the oral viewer 2. The container 3 includes an upper cover 31, a base 32 and a storage space 33. The upper cover 31 is detachably mounted on the base 32, and a space between the upper cover 31 and the base 32 constitutes the storage space 33. The interdental brush 1 and the oral viewer 2 are mounted in the storage space 33.

During oral cleaning, the upper cover 31 is taken down from the base 32, the interdental brush 1 and the oral viewer 2 are taken out from the container 3, and under the assisted observation of the oral viewer 2, tooth gaps are cleaned by using the interdental brush 1. After use, the interdental brush 1 and the oral viewer 2 are disposed in the storage space 33 of the container 3, and then the upper cover 31 is mounted on the base 32, so the oral cleaning kit 800 can constitute a portable and disposable unit again.

The base 32 includes a fixed clamping ring 32-1 and a storage tank 32-2. The fixed clamping ring 32-1 is provided at an open end of the storage tank 32-2. An upper cover connecting mechanism 32-1-1, a rib plate 32-1-3 and a positioning slot hole 32-1-2, connected to the upper cover 31, are provided on the fixed clamping ring 32-1. The upper cover connecting mechanism 32-1-1 is provided at an upper end of the fixed clamping ring 32-1. The positioning slot hole 32-1-2 is provided on the rib plate 32-1-3.

Because the positioning slot hole 32-1-2 is provided on the rib plate 32-1-3, the interdental brush 1 or the oral viewer 2 can be embedded in the positioning slot hole 32-1-2 to be well positioned, so as to prevent an accidental damage to the interdental brush 1 or the oral viewer 2 due to collision between the interdental brush 1 and the oral viewer 2 in a carrying process. By means of the upper cover connecting mechanism 32-1-1, the base 32 can be conveniently connected to the upper cover 31.

The upper cover connecting mechanism 32-1-1 is a concave-convex engaging connection mechanism, a threaded connection mechanism, an interference fit connection mechanism, a hinge connection mechanism, or a buckle connection mechanism, etc. Here, the applicant has only listed the above-mentioned various connection modes, but those skilled in the art may use other connection modes without departing from the scope of protection of the present application.

The base 32 includes a partition plate 32-3. The partition plate 32-3 is distributed along a longitudinal direction of the container 3, and partitions the storage space 33 into a front storage space 33-1 and a rear storage space 33-2. The shape of the lower end of the partition plate 32-3 is matched with that of the positioning slot hole 32-1-2, and the partition plate 32-3 may be conveniently embedded in the positioning slot hole 32-1-2 to form fixing. After the storage space 33 is partitioned into the front storage space 33-1 and the rear storage space 33-2 through the partition plate 32-3, a user may put articles such as the interdental brush 1, the oral viewer 2, a toothbrush 5, toothpaste 6 and dental floss 7 into different storage spaces according to the characteristics of articles for cleaning such as shape and wet-dry state.

The partition plate 32-3 is provided with a positioning slot 32-3-1 and a positioning hook 32-3-2 for fixing the interdental brush 1 or the oral viewer 2. The positioning slot 32-3-1 and the positioning hook 32-3-2 may assist positioning of the interdental brush 1 or the oral viewer 2, so as to better prevent an accidental damage to the interdental brush 1 or the oral viewer 2 due to collision between the interdental brush 1 and the oral viewer 2 in a use process.

The container 3 is provided with a vent 3-1, the vent 3-1 being provided on the base 32. The provision of the vent 3-1 may ensure the evaporation of residual water in the container 3, keep the dryness of the storage space 33 of the container 3, effectively prevent the growth of bacteria, and avoid the residual water from causing short circuit, aging and accidental damage of electronic components, thereby making the oral cleaning kit 800 safer and more hygienic.

The container 3 may contain a toothbrush 5, and/or toothpaste 6, and/or dental floss 7. The container 3 may also contain a daily cleaning product such as a toothbrush 5, and/or toothpaste 6, and/or dental floss 7, and the user may conveniently perform a complete oral cleaning care through the oral cleaning kit of the present disclosure.

The interdental brush 1 is an internal interdental brush 100. The internal interdental brush 100 includes an interdental brush 1, a delivery device 100-2, and the connection mechanism 300; the interdental brush 1 is movably disposed in an elbow 100-2-1 at the front end of the delivery device 100-2; and the connection mechanism 300 is provided on the delivery device 100-2.

The interdental brush 1 of the internal interdental brush 100 includes a working portion 11 and a connecting body 12, the working portion 11 being provided at the front end of the connecting body 12. The delivery device 100-2 includes a guide head 100-21 and a sliding mechanism 100-22. The guide head 100-21 internally includes an elbow 100-2-1. The interdental brush 1 is mounted in the elbow 100-2-1, the working portion 11 of the interdental brush 1 can slide inside the elbow 100-2-1, and the connecting body 12 of the interdental brush 1 is mounted on the sliding mechanism 100-22 of the delivery device 100-2. The movement of the sliding mechanism 100-22 can drive the working portion 11 of the interdental brush 1 to slide in the elbow 100-2-1. By driving the sliding mechanism 100-22, the working portion 11 of the interdental brush 1 can protrude from an outlet of the elbow 100-2-1.

The sliding mechanism 100-22 of the internal interdental brush 100 includes an interdental brush connecting mechanism 100-2-2 and a slider 100-2-3, the interdental brush connecting mechanism 100-2-2 being provided on the slider 100-2-3. The connecting body 12 of the interdental brush and the interdental brush connecting mechanism 100-2-2 are connected together, and the slider 100-2-3 can be pushed and pulled to drive the interdental brush 1 to reciprocate within the elbow 100-2-1, such that the working portion 11 of the interdental brush protrudes or retracts from the outlet of the elbow 100-2-1.

Because the internal interdental brush 100 has a structure of the interdental brush 1 being disposed in the elbow 100-2-1 of the guide head 100-21 of the delivery device 100-2, after the guide head 100-21 aligns to a tooth gap, the working portion 11 of the interdental brush 1 made of an elastic material pushes the sliding mechanism 100-22 on the delivery device 100-2 to drive the working portion 11 of the interdental brush 1 to automatically bend along the curvature of the elbow 100-2-1, and to align and enter the tooth gap. By pushing and pulling the slider 22-2 on the sliding mechanism 100-22 of the delivery device 100-2 back and forth, the working portion 11 of the interdental brush moves back and forth in the tooth gap to clean the tooth gap. Due to the good rigidity of the delivery device 100-2, the working portion 11 of the interdental brush 1 will be pushed out to directly enter the tooth gap after the outlet of the elbow 100-2-1 of the guide head 100-21 of the delivery device 100-2 aligns to the tooth gap. Because the outlet of the elbow 100-2-1 of the guide head 100-21 of the delivery device 100-2 is almost close to the tooth gap, the working portion 11 of the interdental brush is unlikely to bend due to a short distance from the tooth gap, so the conductivity of the power of the interdental brush 1 is greatly improved, the controllability of the interdental brush 1 is improved, and the shortcoming of injury to gums caused by bending of an interdental brush in the prior art when cleaning a gap between molars is avoided.

The internal interdental brush 100 is detachably mounted on the oral viewer 2 through the connection mechanism 300. In this way, the internal interdental brush 100 and the oral viewer 2 may be assembled together to perform a one-handed operation to clean a tooth gap. They may also be separated, that is, the oral observer 2 is held with one hand for observation, and the internal interdental brush 100 is held with the other hand to clean the tooth gap. The user may freely select a use mode according to personal habits.

The interdental brush 1 and the oral viewer 2 are mounted in the front storage space 33-1 of the container 3.

The toothbrush 5, and/or the toothpaste 6, and/or the dental floss 7 are mounted in the rear storage space 33-2.

The upper cover 31 of the container 3 of the oral cleaning kit 800 is a cup capable of holding liquid when tooth brushing. In the cleaning process, the user may use the upper cover 31 as a tooth mug. After use, the upper cover 31 may also be connected to the base 32 to constitute the container 3, thereby being more convenient to use.

The oral cleaning kit 800 includes a holder 4 capable of holding a mobile phone 8. The holder 4 may be provided on the container 3 and used together with the container 3, or may be used alone.

The oral viewer 2 includes an observation system 21. The observation system 21 is a camera system 21-1. Video data of the camera system 21-1 may be transmitted to the mobile phone 8 in a wired or wireless manner. Therefore, by the design of the holder 4, the mobile phone 8 may be conveniently disposed on the container 3, it is unnecessary to hold the mobile phone 8 by hand while cleaning, or the mobile phone 8 is disposed on a wash stand, so as to ensure the convenience, sanitation and hygiene of the use process.

The holder 4 may be fixedly connected to the container 3 or detachably mounted on the container 3. The holder 4 may be fixedly connected to the container 3 by integral manufacturing, bonding, welding, etc., or may be detachably mounted on the container 3 by concave-convex engagement, threaded connection, interference fit, buckle connection, etc.

The holder 4 may be provided at any position of the container 3. The holder 4 may be provided at any position of the upper cover 31 of the container 3, or the bottom, middle or upper part of the base 32.

The holder 4 may be detachably mounted on a bottom 31-1 of the upper cover 31.

The holder 4 includes a support plate 4-1, a housing 4-2, a positioning convex step 4-3, a rotation shaft 4-4, a rotation shaft mounting slot 4-5, and a holder mounting slot 4-6. The support plate 4-1 is provided on the housing 4-2 and is mounted in the rotation shaft mounting slot 4-5 through the rotation shaft 4-4. The mobile phone 8 can be mounted in a space between the positioning convex step 4-3 and the support plate 4-1, the positioning convex step 4-3 can prevent the mobile phone 8 from sliding, and the support plate 4-1 provides support for the mobile phone 8. The holder mounting slot 4-6 can mount the holder 4 on the upper cover 31 of the container 3.

The support plate 4-1 has at least one angle adjustment position.

The support plate 4-1 has a vertical angle adjustment position and an angle adjustment position greater than 90°.

An angle β between the support plate 4-1 of the holder 4 for the mobile phone and an end surface 4-2-1 of the housing 4-2 is continuously adjustable. The user may set different angles β according to personal height and habits.

A groove 4-7 for facilitating the opening of the support plate 4-1 is provided on the housing 4-2 of the holder 4.

In use, the holder 4 may be mounted on the bottom 31-1 of the upper cover 31 of the container 3 through the holder mounting slot 4-6, and the container 3 may be disposed on the wash stand. Or, the holder 4 is directly disposed on the wash stand, the support plate 4-1 is opened through the groove 4-7, the support plate 4-1 is rotated around the rotation shaft 4-4 to the appropriate angle β between the support plate 4-1 and the end surface 4-2-1 of the housing 4-2, and the mobile phone 8 is then disposed in the appropriate positioning convex step 4-3. A video signal transmitted from the camera system 21-1 of the oral viewer 2 is observed through the mobile phone 8 in real time, and immediate and visual tooth or oral cleaning is performed.

An inner surface of the support plate 4-1 of the holder 4 includes a mirror 4-8. The inner surface of the support plate 4-1 of the holder 4 further includes a mirror 4-8, and the user may also directly observe the interior of an oral cavity through the mirror 4-8.

The holder 4 is a drawer-type holder 4 that is provided on the container 3 and can be folded by pushing in and unfolded by pulling out.

The drawer-type holder 4 is disposed on the base 32 of the container 3.

The drawer-type holder 4 is a sliding drawer-type holder. The drawer-type holder 4 further includes a sliding rail 4-9 and a sliding chute 4-10. The sliding rail 4-9 is movable in the sliding chute 4-10. When the drawer-type holder 4 is pulled out, the sliding rail 4-9 protrudes out along the sliding chute 4-10, resulting in that the positioning convex steps 4-3 for mobile phone positioning are sequentially unfolded. The upper part of the base 32 is equivalent to the support plate 4-1 of the holder 4 and constitutes a positioning space for accommodating the mobile phone 8 together with the positioning convex steps 4-3. When the mobile phone 8 is taken away and the housing 4-2 of the holder 4 is pushed inward, the sliding rail 4-9 is retracted into the sliding chute 4-10, and the positioning convex steps 4-3 are sequentially folded and are also folded in the base 32 along with the holder 4.

Because the drawer-type holder 4 is directly provided on the base 32, the base 32 is used to provide support for the mobile phone 8, which is convenient to use. Meanwhile, small cleaning products such as dental floss and cotton swabs may also be disposed in the storage tank 32-2 of the base 32, thereby achieving more complete functions.

The holder 4 is a flip-type holder 4 that is provided on the container 3.

The flip-type holder 4 is disposed on the base 32 of the container 3.

The flip-type holder 4 is an opening-closing flip-type holder. The flip-type holder 4 includes a housing 4-2, a positioning convex step 4-3, a rotation shaft 4-4, a rotation shaft mounting slot 4-5, and a switch buckle position 4-11. After the holder 4 and the base 32 are disconnected by pressing down the switch buckle position 4-11, the holder 4 is rotated around the rotation shaft 4-4, the housing 4-2 may be opened, and the upper part of the base 32 is equivalent to the support plate 4-1 of the holder 4 and constitutes a positioning space for accommodating the mobile phone 8 together with the positioning convex step 4-3. When the mobile phone 8 is taken away, the housing 4-2 is rotated around the opposite direction of the rotation shaft 4-4, and the housing 4-2 is connected and locked to the base 32 through the buckle position 4-11 to fold the holder.

Because the flip-type holder 4 may be directly provided on the base 32 through the rotation shaft 4-4, the housing 4-2 is directly rotated through the rotation shaft 4-4 to unfold or fold the holder 4. The structure is simple, and the use process is also more convenient. Moreover, after the housing 4-2 is opened, cleaning products disposed at the lower part of the storage space 33 may be easily taken out and stored, and the use process is more convenient.

The oral cleaning kit of the present disclosure includes an interdental brush 1, an oral viewer 2 and a container 3. The container 3 includes an upper cover 31, a base 32 and a storage space 33. The base 32 contains a fixed clamping ring 32-1 and a storage tank 32-2, the storage space 33 may be partitioned into a front storage space 33-1 and a rear storage space 33-2 through a partition plate 32-3, and articles such as the interdental brush 1, the oral viewer 2, toothpaste 5 and dental floss 6 may be put into different storage spaces according to the characteristics of the articles. The oral cleaning kit of the present disclosure further includes a holder 4. The holder 4 may be provided on the container 3 and used together with the container 3, or may be used alone. When the holder 4 is unfolded, a mobile phone 8 may be disposed on the holder 4, and the cleaning process may be observed through the mobile phone 8 in real time. The oral cleaning kit of the present disclosure has the advantages of carrying convenience, convenient use and hygiene.

BRIEF DESCRIPTION OF THE DRAWINGS

FIG. 1-1 is an exploded view of FIG. 1.

FIG. 1-2 is an exploded view of FIG. 1.

FIG. 1-3 is an exploded view of FIG. 1.

FIG. 2 is a schematic structural view of an upper cover of an oral cleaning kit of the present disclosure.

FIG. 2-1 is a sectional view of FIG. 2.

FIG. 3 is a three-dimensional structure front view of a base of an oral cleaning kit of the present disclosure.

FIG. 3-1 is a three-dimensional structure rear view of FIG. 3.

FIG. 5-1 is a schematic structure view of an internal interdental brush in FIG. 5 after pushed out.

FIG. 6 is a schematic structural view of an internal interdental brush of an oral cleaning kit of the present disclosure.

FIG. 6-1 is a schematic structure view of an internal interdental brush in FIG. 6 after pushed out.

FIG. 7 is a schematic structural view of an interdental brush of an oral cleaning kit of the present disclosure.

FIG. 8-1 is a structural rear view of FIG. 8.

FIG. 9-1 is a structural bottom view of FIG. 9.

FIG. 12-1 is a three-dimensional structural view of FIG. 12.

FIG. 12-2 is a three-dimensional structural view of an opened support plate in FIG. 12-1.

FIG. 12-3 is an exploded view of FIG. 12-1.

FIG. 12-4 is a three-dimensional structural view of an oral cleaning kit of the present disclosure with a mobile phone disposed on a holder.

FIG. 13-1 is a three-dimensional structural bottom view of FIG. 13.

FIG. 13-2 is a three-dimensional structural view of FIG. 13 with an opened support plate.

FIG. 13-3 is a sectional view of FIG. 13 along A-A.

FIG. 13-4 is a schematic structural view of FIG. 13-3 with a support plate of 90°.

FIG. 13-5 is a schematic structural view of FIG. 13-3 with an angle β between a support plate and an end surface of a housing.

FIG. 16-1 is a sectional view of FIG. 16.

FIG. 16-2 is an exploded view of FIG. 16.

FIG. 16-3 is a schematic structural view of a drawer-type holder in FIG. 16 after unfolded.

FIG. 16-4 is a schematic structural view of a mobile phone disposed on a holder in FIG. 16-3.

FIG. 19-1 is a rear view of FIG. 19.

FIG. 19-2 is a local sectional view of FIG. 19-1.

FIG. 19-3 is an exploded view of FIG. 19-1.

FIG. 20-1 is a schematic assembly view of FIG. 19-1.

In the above drawings:

100. internal interdental brush, 300. connection mechanism, 800. oral cleaning kit of the present disclosure.

1. interdental brush, 2. oral viewer, 3. container, 4. holder, 5. toothbrush, 6. toothpaste, 7. dental floss, 8. mobile phone.

On the internal interdental brush 100:

100-2. delivery device;

11. interdental brush working portion, 12. interdental brush connecting body;

100-21. guide head, 100-2-1. elbow;

100-22. sliding mechanism, 100-2-2. connection mechanism connected to the interdental brush, 100-2-3. slider.

On the oral viewer 2:

21. observation system, 21-1. camera system;

2-1. interdental brush mounting slot.

On the container 3:

31. upper cover, 31-1. bottom of the upper cover, 31-2. positioning convex step of the upper cover;

32. base, 32-1. fixed clamping ring, 32-1-1. upper cover connecting mechanism, 32-1-2. positioning slot hole, 32-1-3. rib plate, 32-2. storage tank, 32-2-1. positioning convex step, 32-3. partition plate, 32-3-1. positioning slot, 32-3-2. positioning hook, 32-3-3. positioning clamping slot, 32-3-4. baffle plate, 32-3-5. limiting convex step, 32-4. positioning slot;

33. storage space, 33-1. front storage space, 33-2. rear storage space;

3-1. vent.

On the holder 4:

4-1. support plate, 4-2. housing, 4-3. positioning convex step, 4-4. rotation shaft, 4-5. rotation shaft mounting slot, 4-6. holder mounting slot, 4-7. groove, 4-8. mirror, 4-9. sliding rail, 4-10. sliding chute, 4-11. switch buckle position, 4-12. limiting plate, 4-13. waterproof step, 4-2-1. end surface of the housing, β is an angle between the support plate and the end surface of the housing.

On the toothbrush:

5-1. toothbrush head, 5-2. host.

On the dental floss:

7-1. connection mechanism, 7-2. working portion.

DESCRIPTION OF EMBODIMENTS

Embodiment 1: An Oral Cleaning Kit of the Present Disclosure

Figure 1:
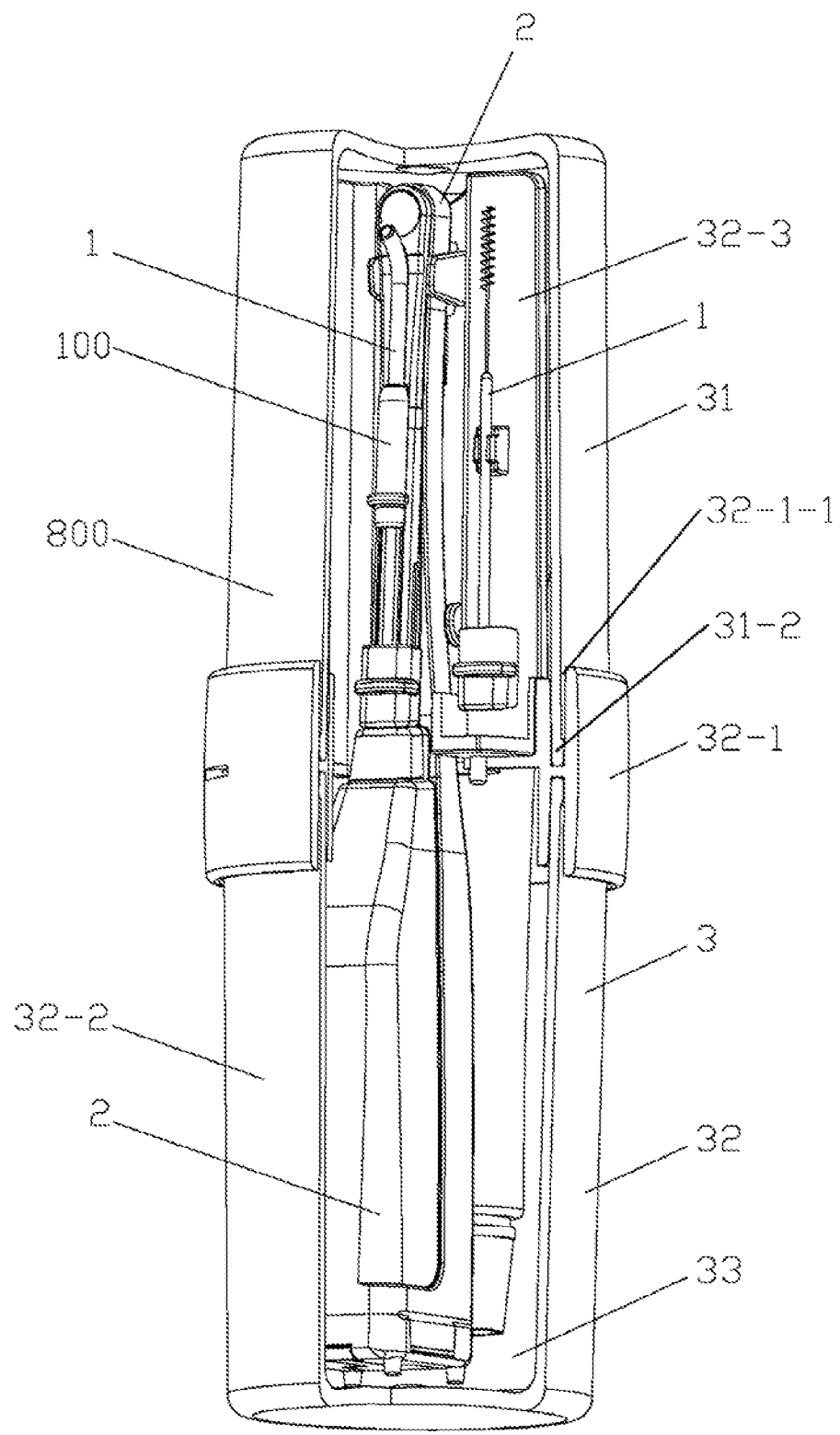
FIG. 1 is a schematic structural view of an oral cleaning kit of the present disclosure.
Figure 1:
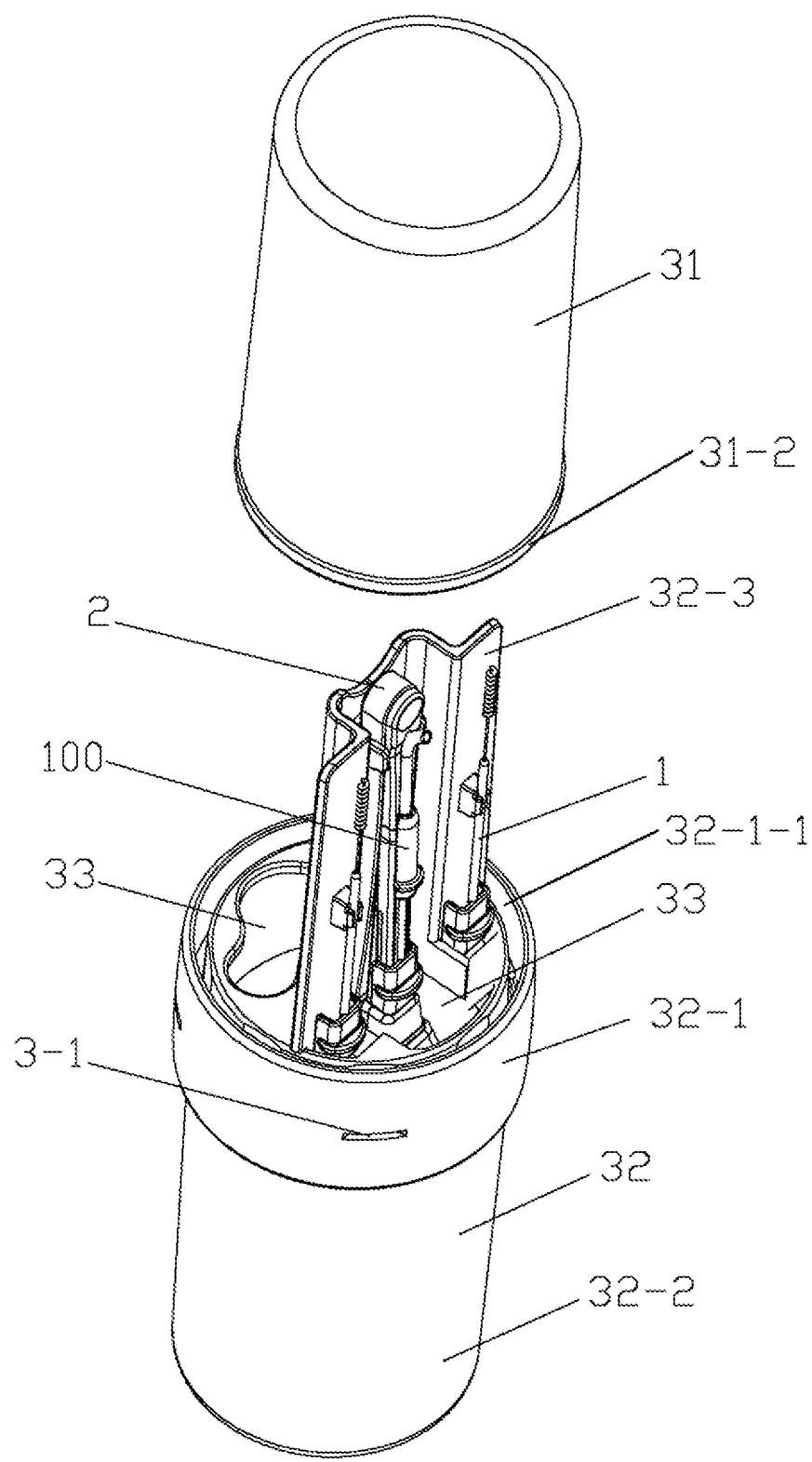
Figures 1, 2:
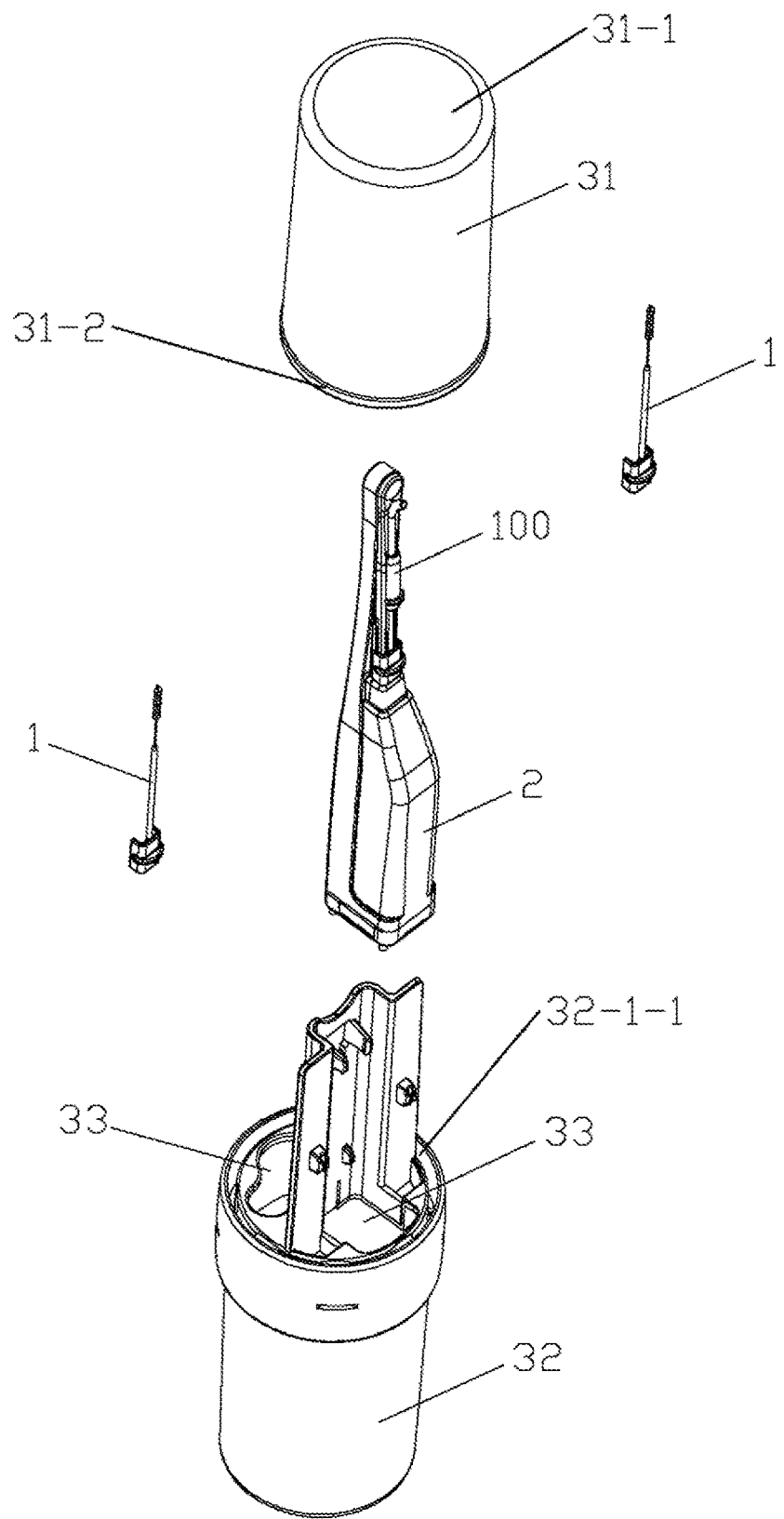
Figures 1, 2, 3:
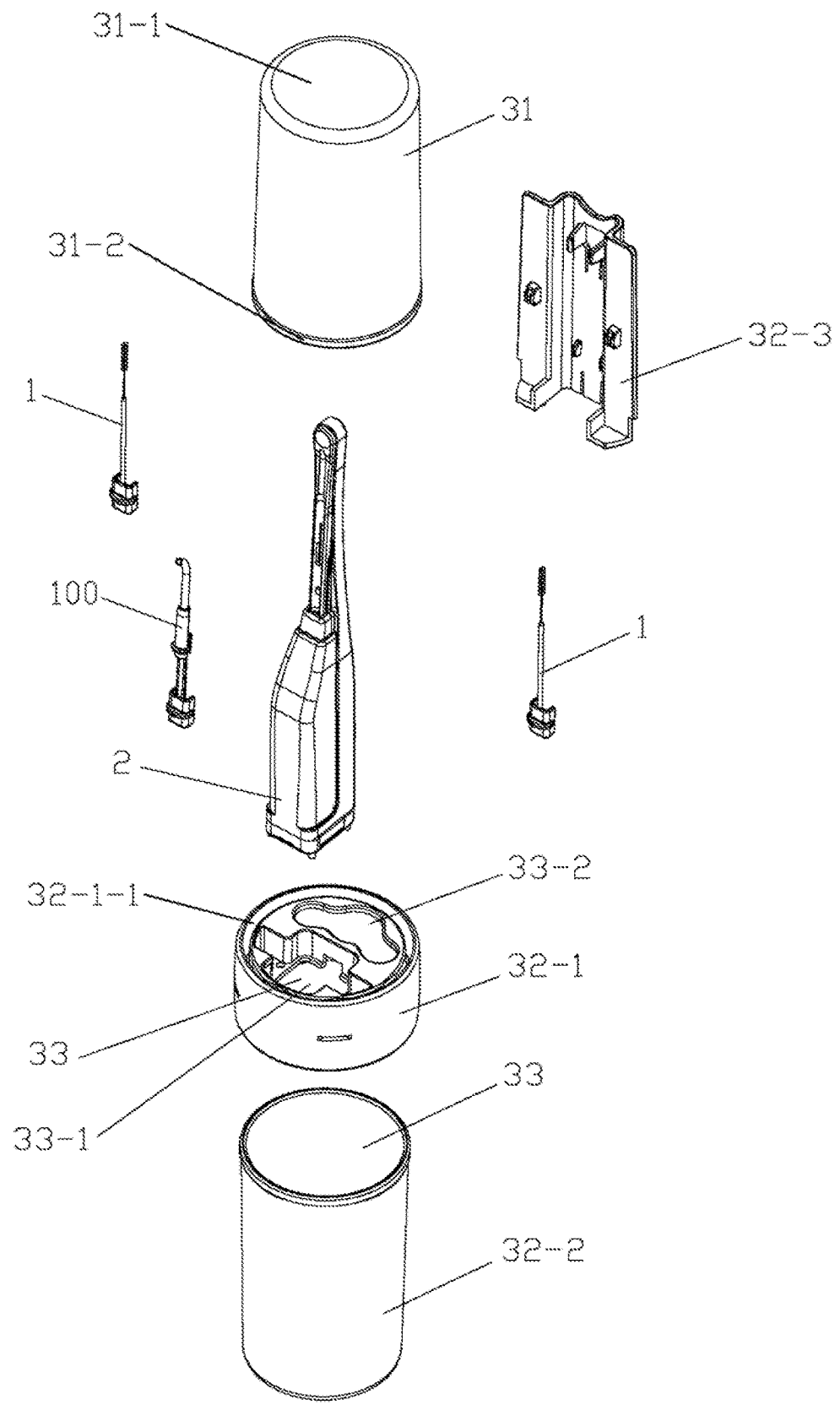
Figure 2:
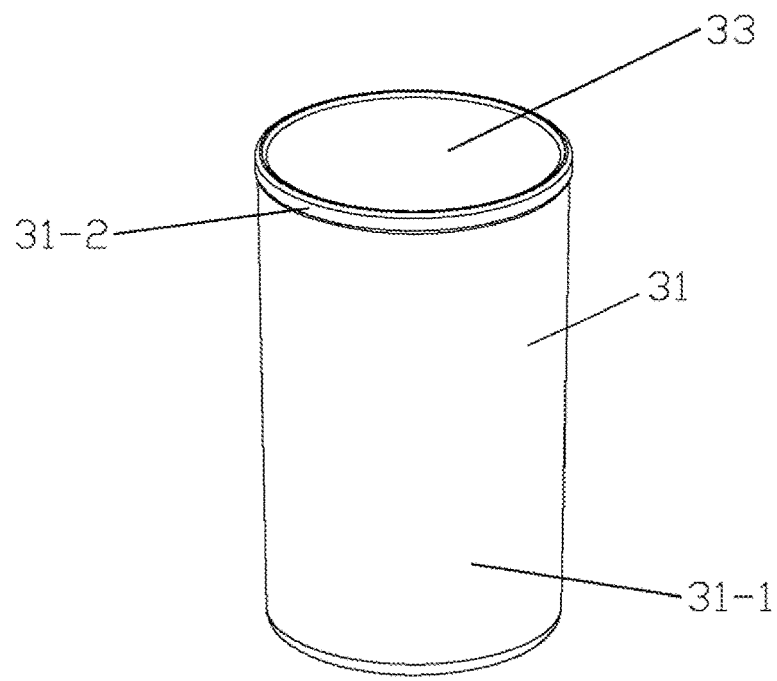
Figures 1, 2:
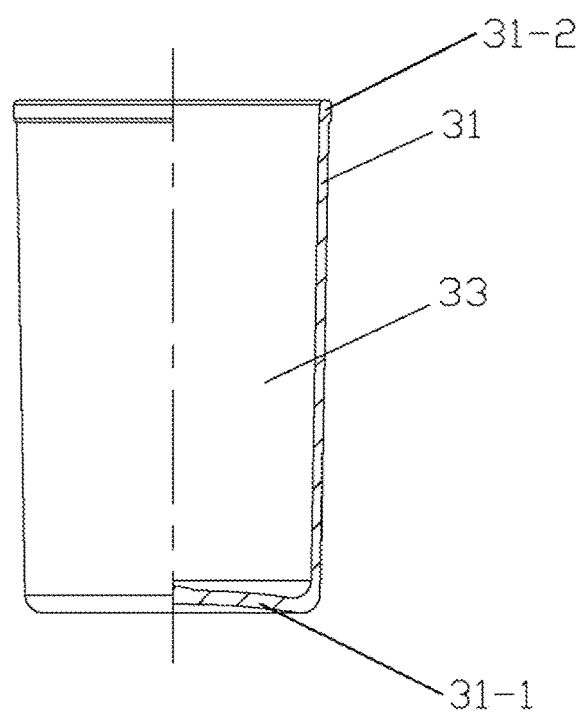
Figure 3:
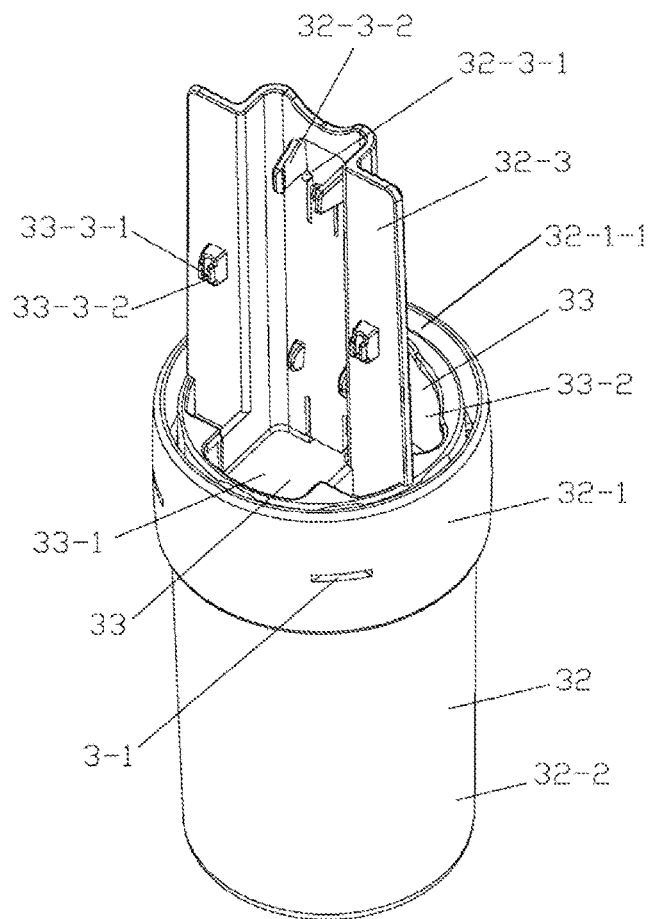
Figures 1, 3:
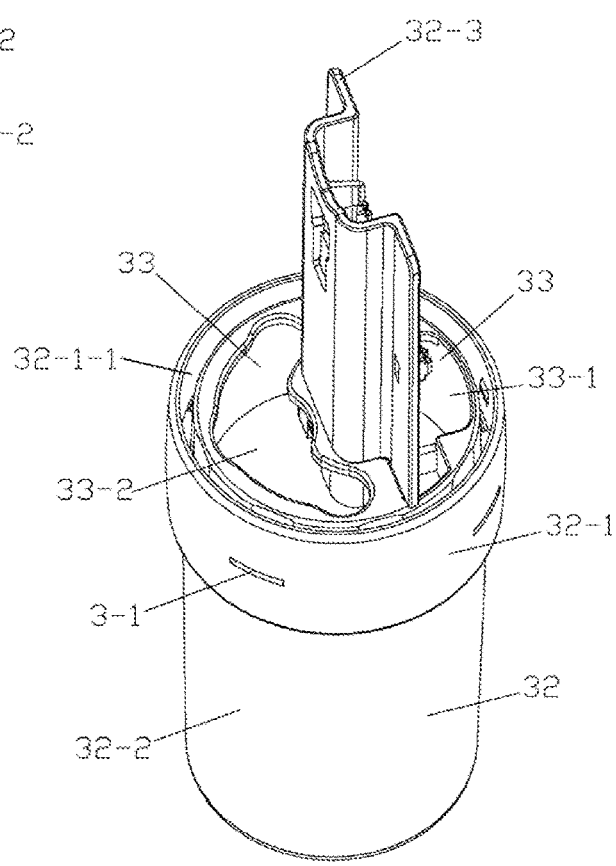

Referring to FIG. 1 to FIG. 1-3, an oral cleaning kit 800 of the present disclosure includes an interdental brush 1, an oral viewer 2, and a container 3 capable of containing the interdental brush 1 and the oral viewer 2.

In the present embodiment, the container 3 includes an upper cover 31, a base 32 and a storage space 33. The upper cover 31 is detachably mounted on the base 32, and a space between the upper cover 31 and the base 32 constitutes the storage space 33. The interdental brush 1 and the oral viewer 2 are mounted in the storage space 33.

Referring to FIG. 1 to FIG. 2-1, in the present embodiment, the upper cover 31 is connected to the base 32 in a concave-convex engagement manner. The upper cover includes a positioning convex step 31-2, and the base 32 includes a groove-type upper cover connecting mechanism 32-1-1. The positioning convex step 31-2 of the upper cover is embedded in a groove of the upper cover connecting mechanism 32-1-1 of the base 32 to form a concave-convex engaging connection.

Referring to FIG. 9 to FIG. 11, and FIG. 3 to FIG. 3-1, the base 32 includes a fixed clamping ring 32-1 and a storage tank 32-2.

The fixed clamping ring 32-1 is provided at an open end of the storage tank 32-2. An upper cover connecting mechanism 32-1-1, a rib plate 32-1-3 and a positioning slot hole 32-1-2, connected to the upper cover 31, are provided on the fixed clamping ring 32-1. The upper cover connecting mechanism 32-1-1 is provided at an upper end of the fixed clamping ring 32-1. The positioning slot hole 32-1-2 is provided on the rib plate 32-1-3.

In the present embodiment, the fixed clamping ring 32-1 and the storage tank 32-2 are connected together in a concave-convex engagement manner. When the base 32 is cleaned, the fixed clamping ring 32-1 may be taken down from the storage tank 32-2. The cleaning is more convenient.

Figure 17:
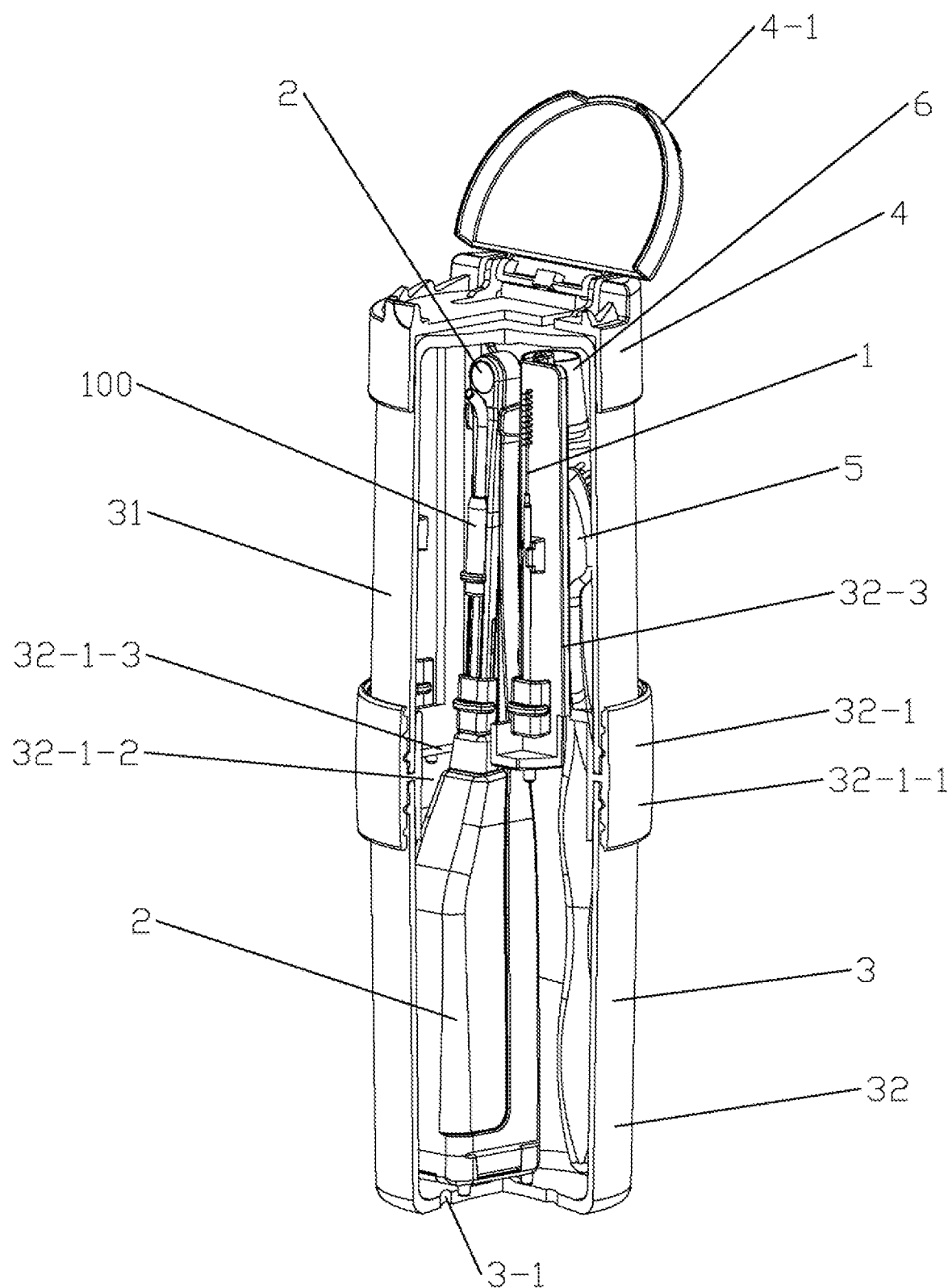
FIG. 17 is a schematic structural view of a threaded connection type oral cleaning kit of the present disclosure.

Of course, the fixed clamping ring 32-1 and the storage tank 32-2 may also be connected in a threaded connection manner, referring to FIG. 17. In the embodiment shown in FIG. 17, the storage tank 32-2 and the fixed clamping ring 32-1 are detachably connected through threads.

Figure 18:
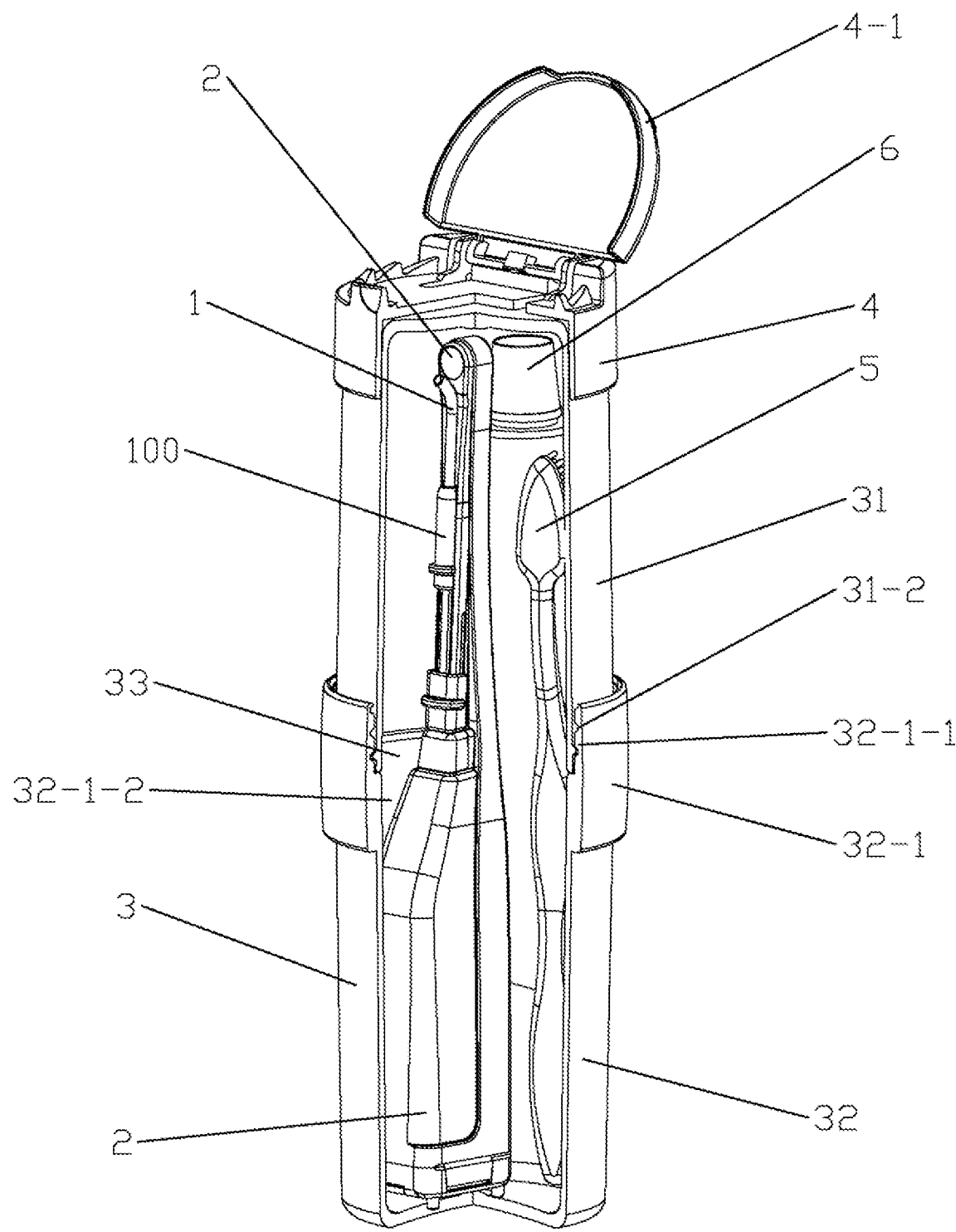
FIG. 18 is a schematic structural view of a threaded connection type oral cleaning kit of the present disclosure without a partition plate.

In addition, the fixed clamping ring 32-1 and the storage tank 32-2 may be integrally manufactured, referring to FIG. 18. In the embodiment shown in FIG. 18, the fixed clamping ring 32-1 is an internal thread, provided in the storage tank 32-2, and forms the thread-type upper cover connecting mechanism 32-1-1 with an external thread convex step 31-2 on the open end of the upper cover 31. The difference between the embodiment shown in FIG. 18 and the embodiment shown in FIG. 17 lies in that: the fixed clamping ring 32-1 of the embodiment shown in FIG. 17 is provided with a rib plate 32-1-3 and a positioning slot hole 32-1-2, while the fixed clamping ring 32-1 of the embodiment shown in FIG. 18 is not provided with the rib plate 32-1-3 and is only provided with the positioning slot hole 32-1-2, set as a through hole. In addition, the vent 3-1 for keeping the dryness of the container 3 is also provided at the bottom of the storage tank 32-2 to facilitate drainage and exhaust.

The connection manner between the fixed clamping ring 32-1 and the storage tank 32-2 may be a fixed connection or a detachable connection such as a concave-convex engaging connection, a buckle connection, or an interference fit connection. They may be connected together non-detachably by integral manufacturing, welding or bonding without departing from the scope of protection of the present application.

Referring to FIG. 1 to FIG. 11, in the present embodiment, the upper cover connecting mechanism 32-1-1 is a concave-convex engaging connection mechanism, the positioning convex step 31-2 of the upper cover 31 is embedded in a groove of the upper cover connecting mechanism 32-1-1, and the upper cover 31 and the fixed clamping ring 32-1 may be connected together.

Of course, the upper cover connecting mechanism 32-1-1 may also be a threaded connection mechanism, referring to FIG. 17 to FIG. 18. In the embodiments shown in FIG. 17 and FIG. 18, the upper cover 31 and the base 32 are detachably connected together in a threaded connection manner.

In addition, the upper cover 31 and the base 32 may also be connected through multiple manners such as an interference fit connection mechanism, a hinge connection mechanism, a buckle connection mechanism or other connection mechanisms without departing from the scope of protection of the present application.

Because the positioning slot hole 32-1-2 is provided on the rib plate 32-1-3, the interdental brush 1 or the oral viewer 2 can be embedded in the positioning slot hole 32-1-2 to be well positioned, so as to prevent an accidental damage to the interdental brush 1 or the oral viewer 2 due to collision between the interdental brush 1 and the oral viewer 2 in a carrying process. By means of the upper cover connecting mechanism 32-1-1, the base 32 can be conveniently connected to the upper cover 31.

Referring to FIG. 3 and FIG. 3-1, the base 32 further includes a partition plate 32-3.

The partition plate 32-3 is distributed along a longitudinal direction of the container 3, and partitions the storage space 33 into a front storage space 33-1 and a rear storage space 33-2. The shape of the lower end of the partition plate 32-3 is matched with that of the positioning slot hole 32-1-2, and the partition plate 32-3 may be conveniently embedded in the positioning slot hole 32-1-2 to form fixing. After the storage space 33 is partitioned into the front storage space 33-1 and the rear storage space 33-2 through the partition plate 32-3, a user may put articles into different storage spaces according to the characteristics of articles for cleaning such as shape and wet-dry state. For example, the interdental brush 1 and the oral viewer 2 are mounted in the front storage space 33-1 of the container 3; and the toothbrush 5, and/or the toothpaste 6, and/or the dental floss 7 are mounted in the rear storage space 33-2, referring to FIG. 14 and FIG. 15.

Figure 8:
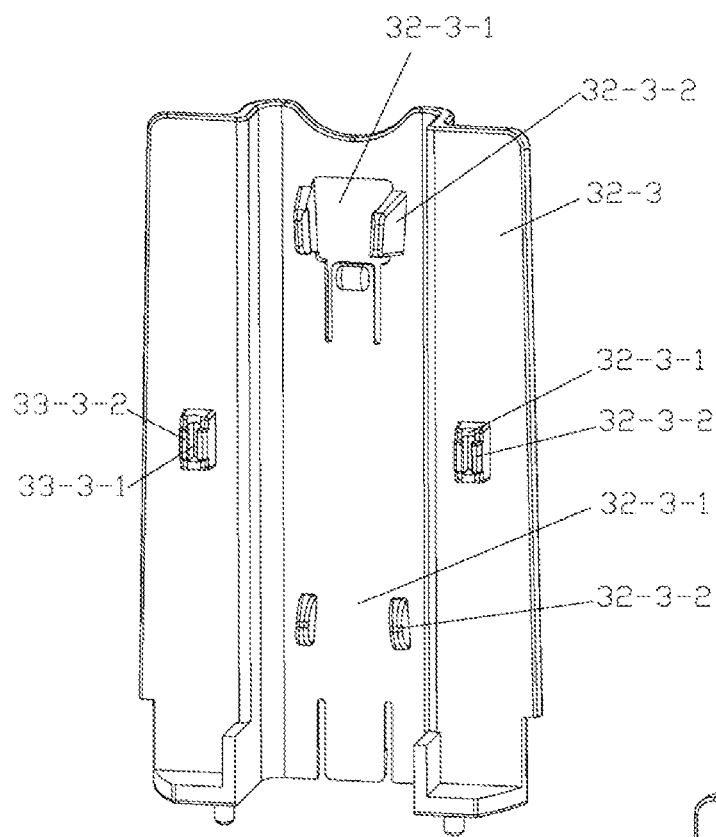
FIG. 8 is a structural front view of a partition plate of an oral cleaning kit of the present disclosure.
Figures 1, 8:
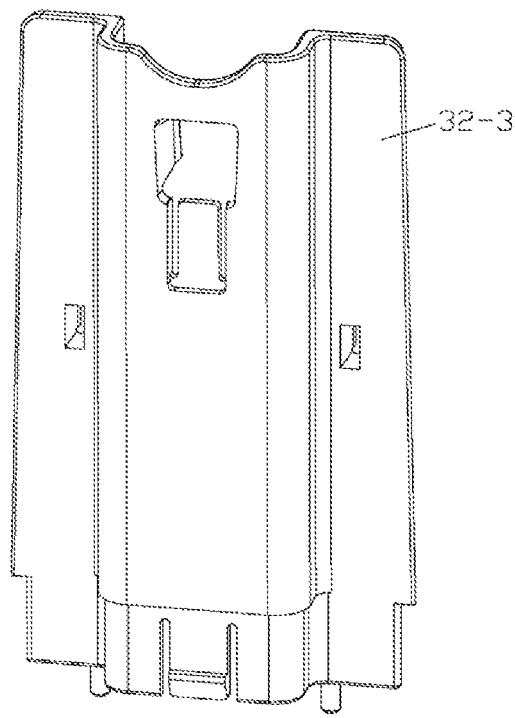
Figure 9:
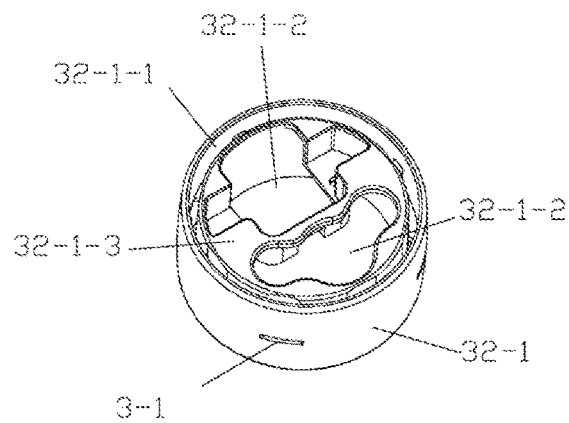
FIG. 9 is a structural top view of a fixed clamping ring of an oral cleaning kit of the present disclosure.
Figures 1, 9:
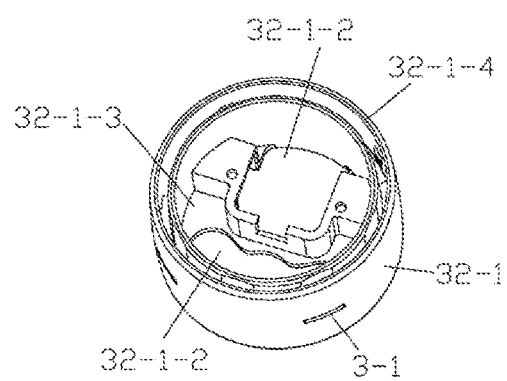
Figure 10:
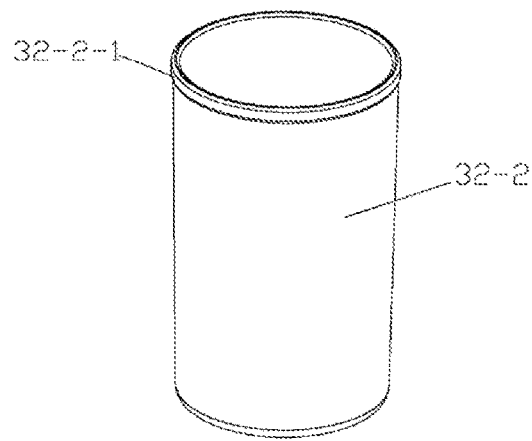
FIG. 10 is a three-dimensional structural view of a storage tank of an oral cleaning kit of the present disclosure.
Figure 11:
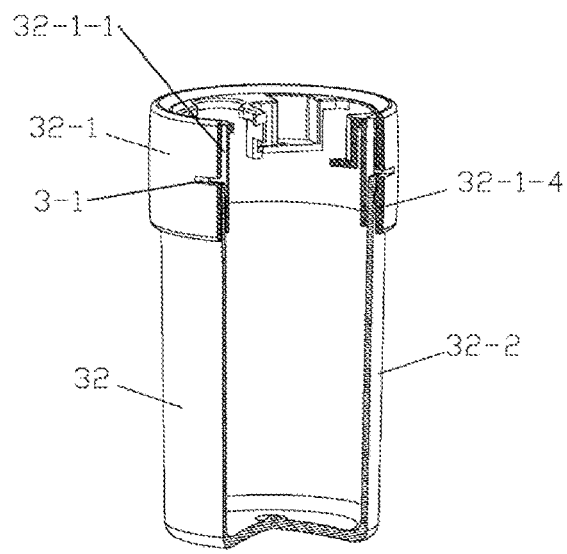
FIG. 11 is a schematic structural view of a base of an oral cleaning kit of the present disclosure.

Referring to FIG. 8 and FIG. 8-1, the partition plate 32-3 is provided with a positioning slot 32-3-1 and a positioning hook 32-3-2 for fixing the interdental brush 1 or the oral viewer 2. The positioning slot 32-3-1 and the positioning hook 32-3-2 may further assist positioning of the interdental brush 1 or the oral viewer 2, so as to better prevent an accidental damage to the interdental brush 1 or the oral viewer 2 due to collision between the interdental brush 1 and the oral viewer 2 in a carry or use process.

Referring to FIG. 1 to FIG. 3-1, the upper cover 31 of the container 3 is a cup capable of holding liquid when tooth brushing. In the cleaning process, the user may use the upper cover 31 as a tooth mug. After use, the upper cover 31 may be connected to the base 32 again to constitute the container 3, thereby being more convenient to use.

The container 3 is provided with a vent 3-1, the vent 3-1 being provided on the base 32. The provision of the vent 3-1 may ensure the evaporation of residual water in the container 3, keep the dryness of the storage space 33 of the container 3, effectively prevent the growth of bacteria, and avoid the residual water from causing short circuit, aging and accidental damage of electronic components, thereby making the oral cleaning kit 800 safer and more hygienic.

Referring to FIG. 6 to FIG. 7, in the present embodiment, the interdental brush 1 includes an internal interdental brush 100. The internal interdental brush 100 includes an interdental brush 1, a delivery device 100-2, and a connection mechanism 300; the interdental brush 1 is movably disposed in an elbow 100-2-1 at the front end of the delivery device 100-2; and the connection mechanism 300 is provided on the delivery device 100-2.

The interdental brush 1 of the internal interdental brush 100 includes a working portion 11 and a connecting body 12, the working portion 11 being provided at the front end of the connecting body 12. The delivery device 100-2 includes a guide head 100-21 and a sliding mechanism 100-22. The guide head 100-21 internally includes an elbow 100-2-1. The interdental brush 1 is mounted in the elbow 100-2-1, the working portion 11 of the interdental brush 1 can slide inside the elbow 100-2-1, and the connecting body 12 of the interdental brush 1 is mounted on the sliding mechanism 100-22 of the delivery device 100-2. The movement of the sliding mechanism 100-22 can drive the working portion 11 of the interdental brush 1 to slide in the elbow 100-2-1. By driving the sliding mechanism 100-22, the working portion 11 of the interdental brush 1 can protrude from an outlet of the elbow 100-2-1.

The sliding mechanism 100-22 of the internal interdental brush 100 includes an interdental brush connecting mechanism 100-2-2 and a slider 100-2-3, the interdental brush connecting mechanism 100-2-2 being provided on the slider 100-2-3. The connecting body 12 of the interdental brush and the interdental brush connecting mechanism 100-2-2 are connected together, and the slider 100-2-3 can be pushed and pulled to drive the interdental brush 1 to reciprocate within the elbow 100-2-1, such that the working portion 11 of the interdental brush protrudes or retracts from the outlet of the elbow 100-2-1, referring to FIG. 6 to FIG. 7.

Because the internal interdental brush 100 has a structure of the interdental brush 1 being disposed in the elbow 100-2-1 of the guide head 100-21 of the delivery device 100-2, after the guide head 100-21 aligns to a tooth gap, the working portion 11 of the interdental brush 1 made of an elastic material pushes the sliding mechanism 100-22 on the delivery device 100-2 to drive the working portion 11 of the interdental brush 1 to automatically bend along the curvature of the elbow 100-2-1, and to align and enter the tooth gap. By pushing and pulling the slider 100-2-3 on the sliding mechanism 100-22 of the delivery device 100-2 back and forth, the working portion 11 of the interdental brush moves back and forth in the tooth gap to clean the tooth gap. Due to the good rigidity of the delivery device 100-2, the working portion 11 of the interdental brush 1 will be pushed out to directly enter the tooth gap after the outlet of the elbow 100-2-1 of the guide head 100-21 of the delivery device 100-2 aligns to the tooth gap. Because the outlet of the elbow 100-2-1 of the guide head 100-21 of the delivery device 100-2 is almost close to the tooth gap, the working portion 11 of the interdental brush is unlikely to bend due to a short distance from the tooth gap, so the conductivity of the interdental brush 1 is greatly improved, the controllability of the interdental brush 1 is improved, and the shortcoming of injury to gums caused by bending of an interdental brush in the prior art when cleaning a gap between molars is avoided.

Figure 4:
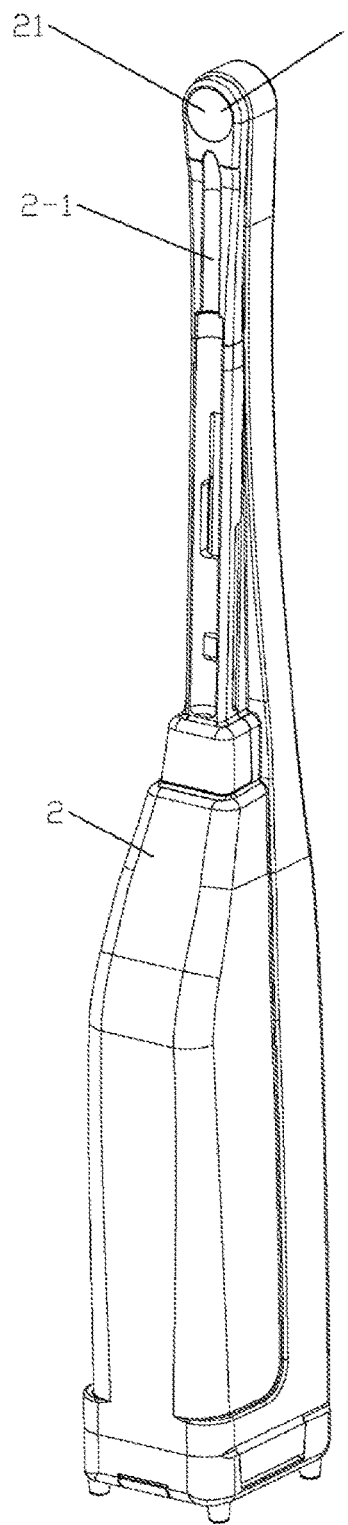
FIG. 4 is a schematic structural view of an oral viewer of an oral cleaning kit of the present disclosure.
Figure 5:
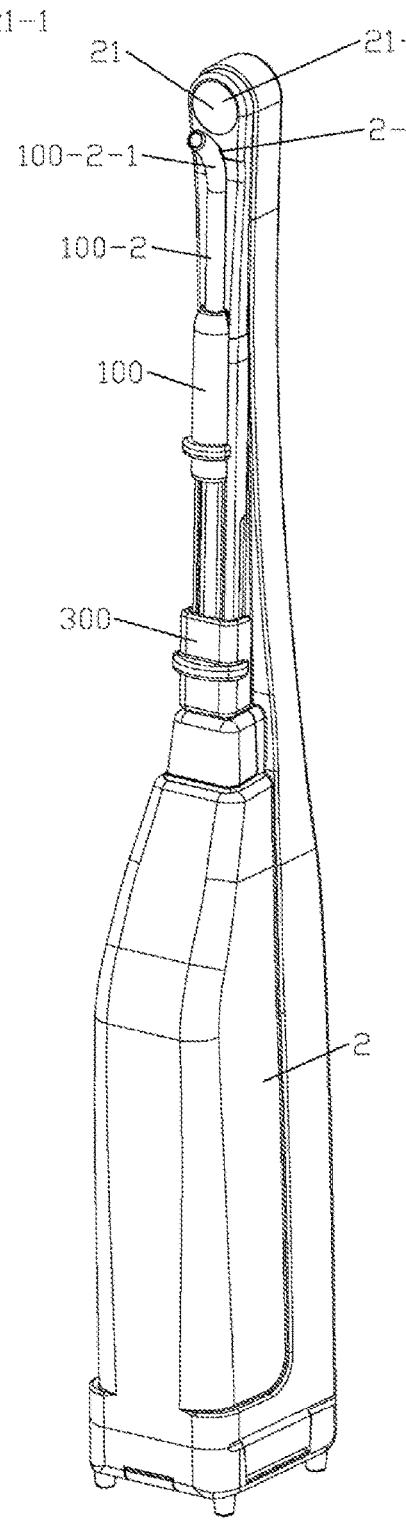
FIG. 5 is a schematic structural view of mounting an internal interdental brush on an oral viewer of an oral cleaning kit of the present disclosure.
Figure 1:
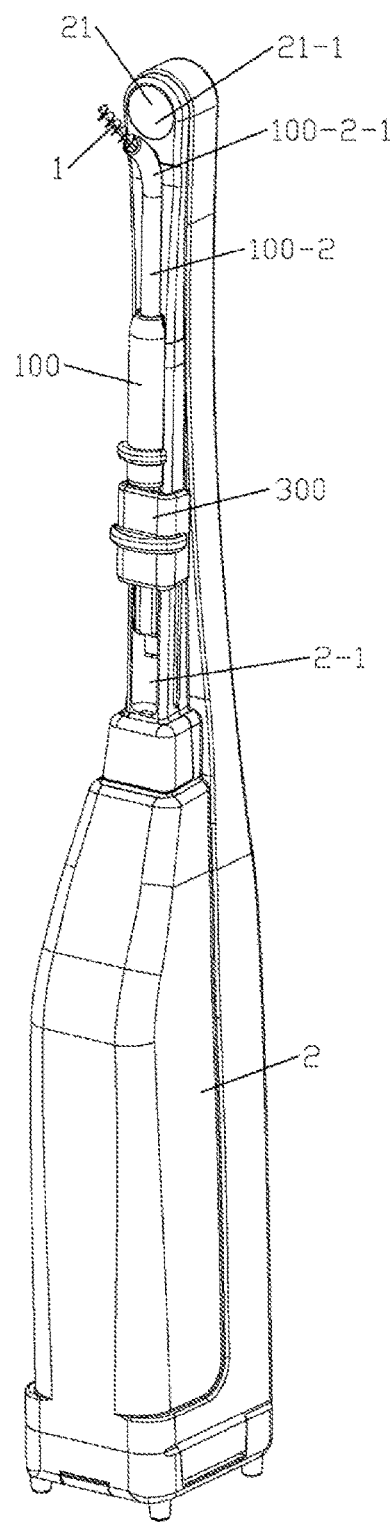

Referring to FIG. 4 to FIG. 5-1, the internal interdental brush 100 is detachably mounted in the interdental brush mounting slot 2-1 of the oral viewer 2 through the connection mechanism 300. In this way, the internal interdental brush 100 and the oral viewer 2 may be assembled together to perform a one-handed operation to clean a tooth gap. They may also be separated, that is, the oral observer 2 is held with one hand for observation, and the internal interdental brush 100 is held with the other hand to clean the tooth gap. The user may freely select a use mode according to personal habits.

The oral viewer 2 includes an observation system 21. The observation system 21 is a camera system 21-1. Video data of the camera system 21-1 may be transmitted to the mobile phone 8 in a wired or wireless manner, and the oral cleaning process may be observed in real time.

During oral cleaning, the upper cover 31 is taken down from the base 32, the interdental brush 1 and the oral viewer 2 are taken out from the container 3, and under the assisted observation of the oral viewer 2, tooth gaps are cleaned by using the interdental brush 1. After use, the interdental brush 1 and the oral viewer 2 are disposed in the storage space 33 of the container 3, and then the upper cover 31 is mounted on the base 32, so the oral cleaning kit 800 can constitute a portable and disposable unit again. The oral cleaning kit of the present disclosure has the advantages of carrying convenience, convenient use and hygiene.

Embodiment 2: An Oral Cleaning Kit of the Present Disclosure with a Holder

Figure 12:
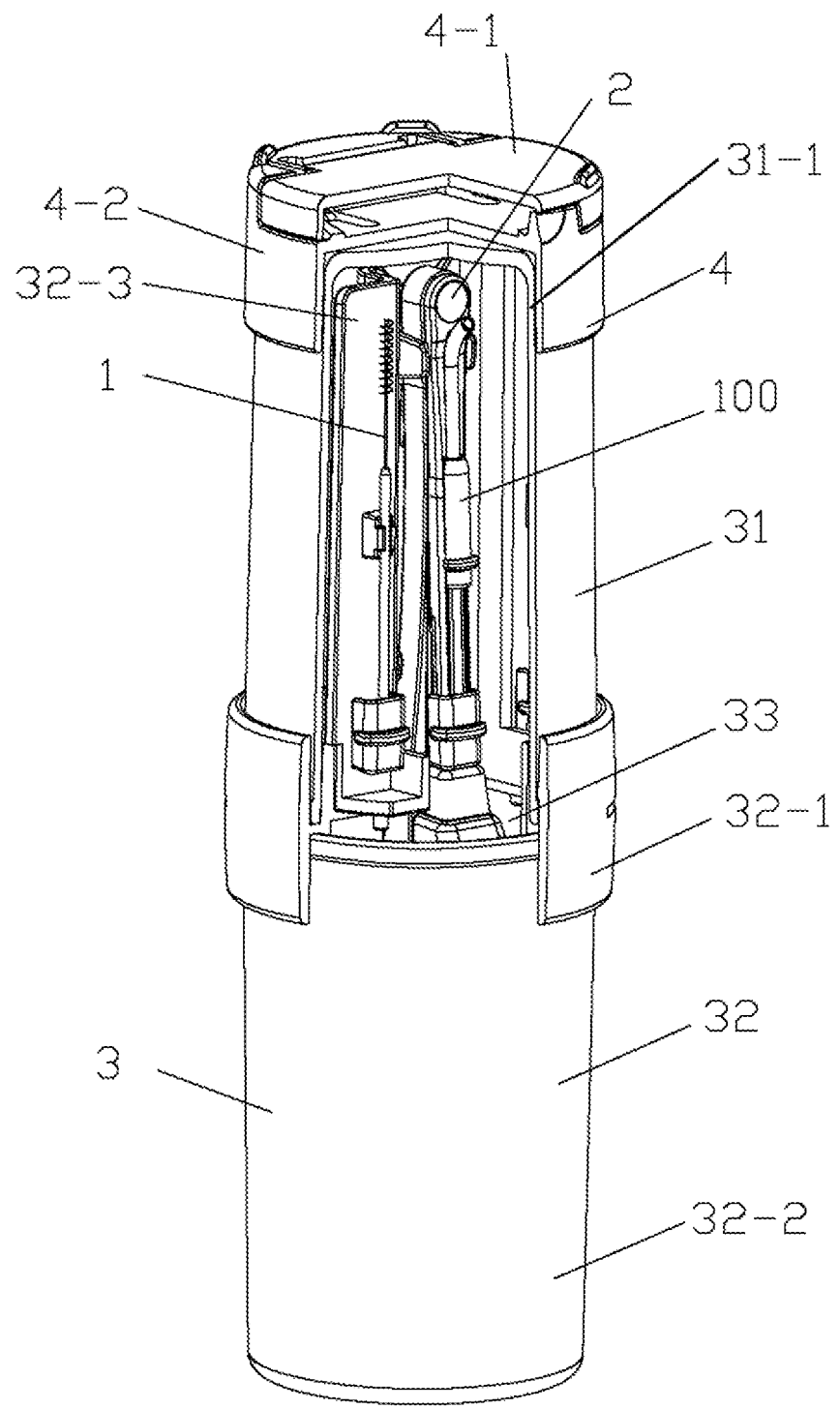
FIG. 12 is a schematic structural view of an oral cleaning kit of the present disclosure with a mobile phone holder.
Figures 1, 12:
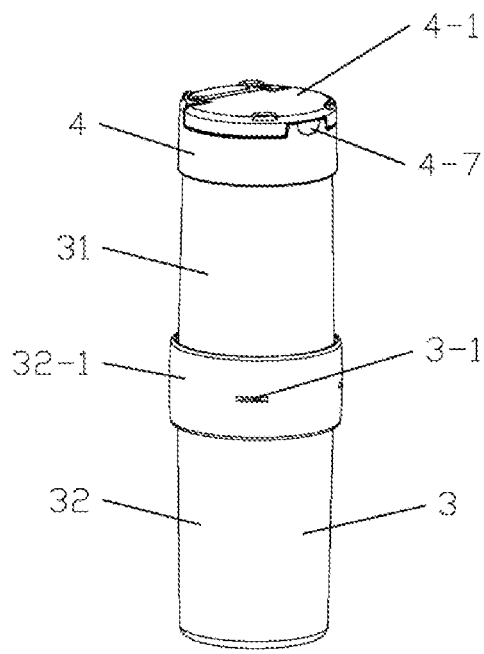
Figures 2, 12:
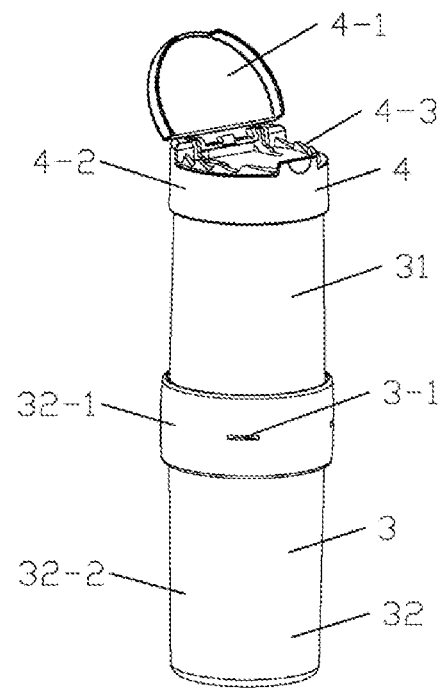
Figures 3, 12:
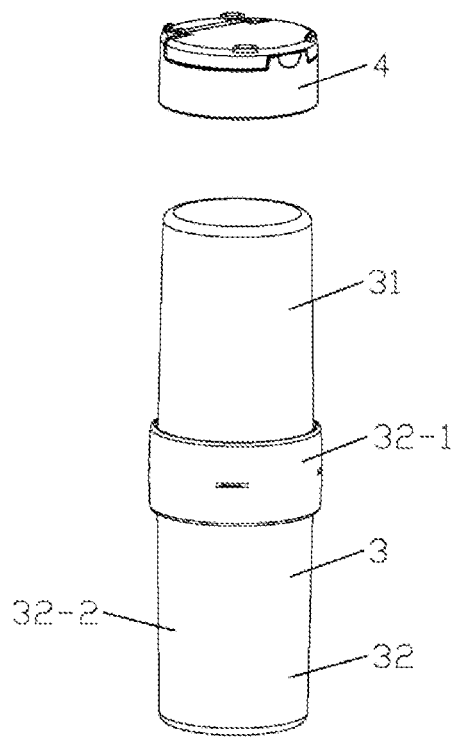
Figures 4, 12:
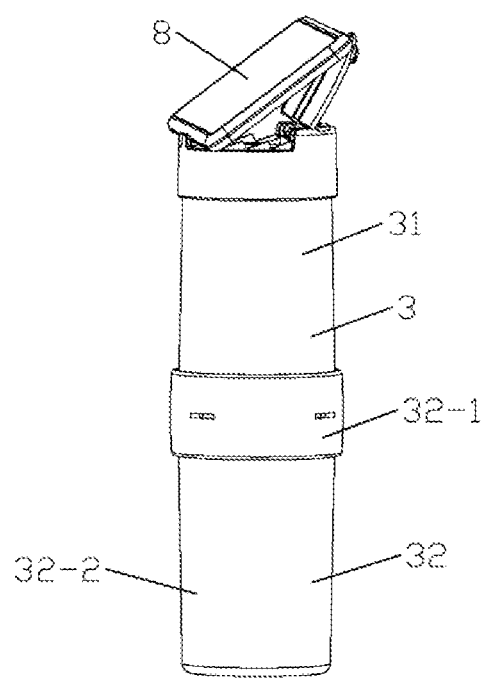
Figure 13:
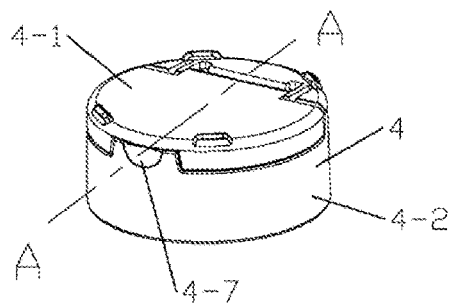
FIG. 13 is a three-dimensional structure top view of a holder of an oral cleaning kit of the present disclosure.
Figures 1, 13:
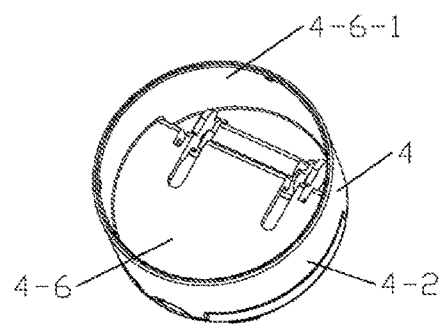
Figures 2, 13:
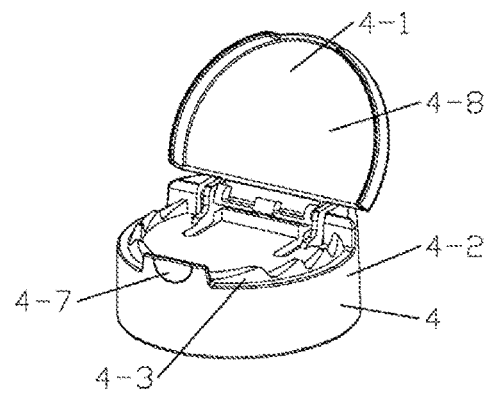
Figures 3, 13:
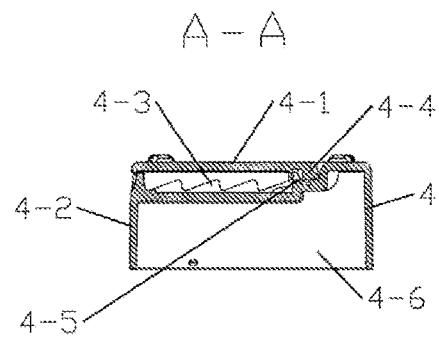
Figures 4, 13:
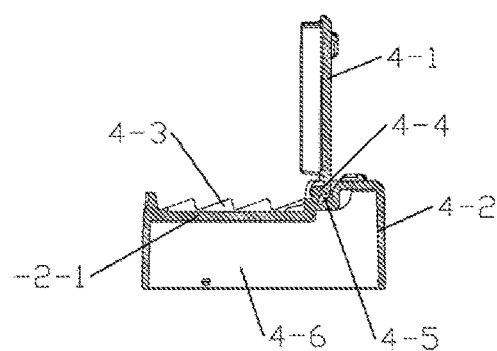
Figures 5, 13:
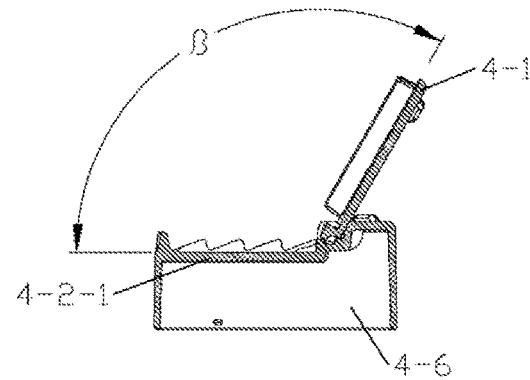
Figure 14:
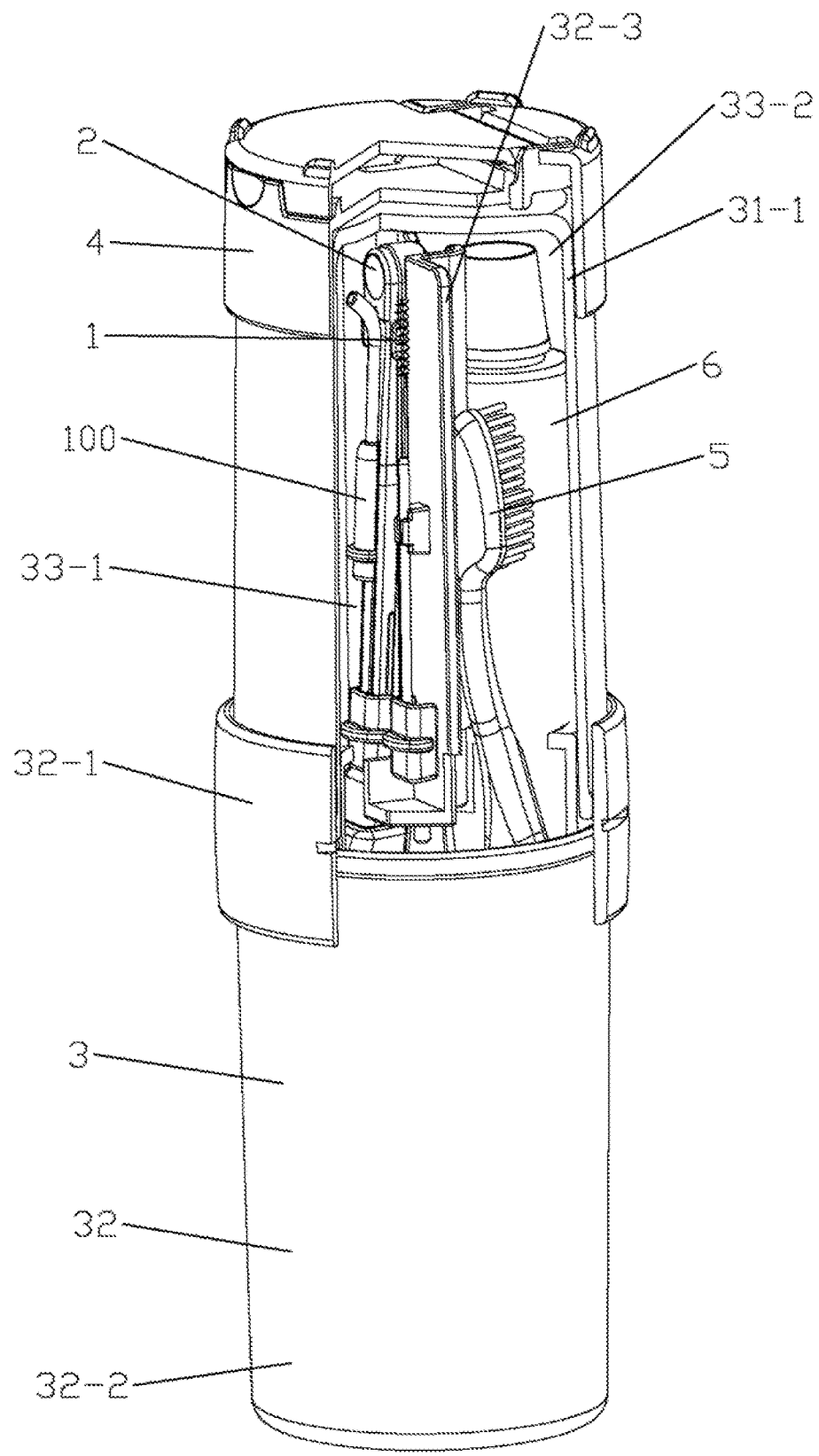
FIG. 14 is a schematic structural view of an oral cleaning kit of the present disclosure with toothpaste and a toothbrush.
Figure 15:
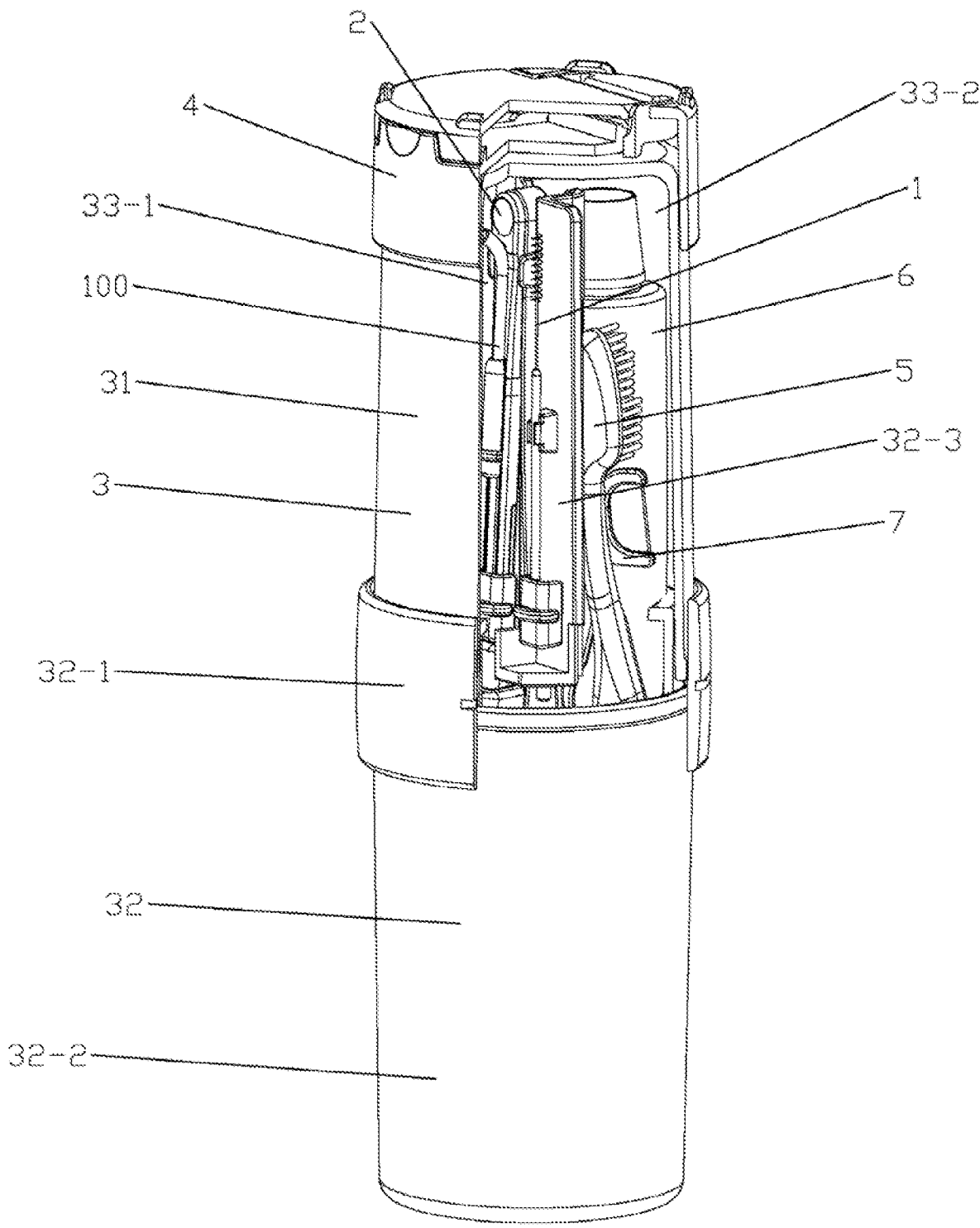
FIG. 15 is a schematic structural view of an oral cleaning kit of the present disclosure with toothpaste, a toothbrush and dental floss.

Referring to FIG. 12 to FIG. 14, the difference between the present embodiment and Embodiment 1 lies in that: in the present embodiment, the oral cleaning kit 800 further includes a holder 4 for holding a mobile phone 8.

The holder 4 may be provided on the container 3 and used together with the container 3, or may be used alone. In the present embodiment, the holder 4 may be detachably mounted on a bottom 31-1 of the upper cover 31 in a concave-convex engagement manner, referring to FIG. 12 to FIG. 12-4.

The holder 4 may also be fixedly connected to the container 3 by integral manufacturing, bonding, welding, etc., or may be detachably mounted on the container 3 by threaded connection, interference fit, buckle connection, etc., without departing from the scope of protection of the present application.

Referring to FIG. 13 to FIG. 13-5, the holder 4 includes a support plate 4-1, a housing 4-2, a positioning convex step 4-3, a rotation shaft 4-4, a rotation shaft mounting slot 4-5, and a holder mounting slot 4-6. The support plate 4-1 is provided on the housing 4-2 and is mounted in the rotation shaft mounting slot 4-5 through the rotation shaft 4-4. The mobile phone 8 can be mounted in a space between the positioning convex step 4-3 and the support plate 4-1, the positioning convex step 4-3 can prevent the mobile phone 8 from sliding, and the support plate 4-1 provides support for the mobile phone 8. The holder mounting slot 4-6 can mount the holder 4 on the upper cover 31 of the container 3.

Referring to FIG. 13-4 and FIG. 13-5, the support plate 4-1 has at least one angle adjustment position. In the present embodiment, the support plate 4-1 has a vertical angle adjustment position and an angle adjustment position greater than 90°. An angle β between the support plate 4-1 of the holder 4 for the mobile phone and an end surface 4-2-1 of the housing 4-2 is continuously adjustable.

In the present embodiment, multiple positioning convex steps 4-3 are provided on the holder 4, and may adjust an inclination angle of the mobile phone 8 to meet requirements of users with different heights and use habits.

A groove 4-7 for facilitating the opening of the support plate 4-1 is provided on the housing 4-2 of the holder 4.

In use, the holder 4 may be mounted on the bottom 31-1 of the upper cover 31 of the container 3 through the holder mounting slot 4-6, the container 3 is disposed on a wash stand, the support plate 4-1 is opened through the groove 4-7, the support plate 4-1 is rotated around the rotation shaft 4-4 to an appropriate angle β between the support plate 4-1 and the end surface 4-2-1 of the housing 4-2, and the mobile phone 8 is then disposed in the appropriate positioning convex step 4-3. A video signal transmitted from the camera system 21-1 of the oral viewer 2 is observed through the mobile phone 8 in real time.

The holder 4 may also be provided at any position of the upper cover 31 of the container 3, or the bottom, middle or upper part of the base 32. The holder 4 may also be used alone, the holder 4 is directly disposed on the wash stand, and the mobile phone 8 is disposed on the holder 4. At this time, the upper cover 31 may still be used as a tooth mug, and the use process is more convenient.

The inner surface of the support plate 4-1 of the holder 4 further includes a mirror 4-8, and a user may also directly observe the interior of an oral cavity through the mirror 4-8.

By the design of the holder 4, the mobile phone 8 may be conveniently disposed on the container 3, it is unnecessary to hold the mobile phone 8 by hand while cleaning, or the mobile phone 8 is disposed on the wash stand, so as to ensure the convenience, sanitation and hygiene of the use process.

Embodiment 3: An Oral Cleaning Kit of the Present Disclosure with a Drawer-Type Holder Referring to FIG. 16 to FIG. 16-4, the difference between the present embodiment and Embodiment 2 lies in that: in the present embodiment, the holder 4 is a drawer-type holder.

In the present embodiment, the upper cover 31 and the fixed clamping ring 32-1 are connected in a buckle connection manner. During connection, the upper cover connecting mechanism 32-1-1 is buckled on the positioning convex step 31-2 of the upper cover 31. When the upper cover 31 is taken down, the upper cover connecting mechanism 32-1-1 is opened to both sides, and the upper cover 31 may be easily taken down, referring to FIG. 16 to FIG. 16-4.

The holder 4 is a drawer-type holder 4 that is provided on the container 3 and can be folded by pushing in and unfolded by pulling out.

The drawer-type holder 4 is disposed on the base 32 of the container 3.

Figure 16:
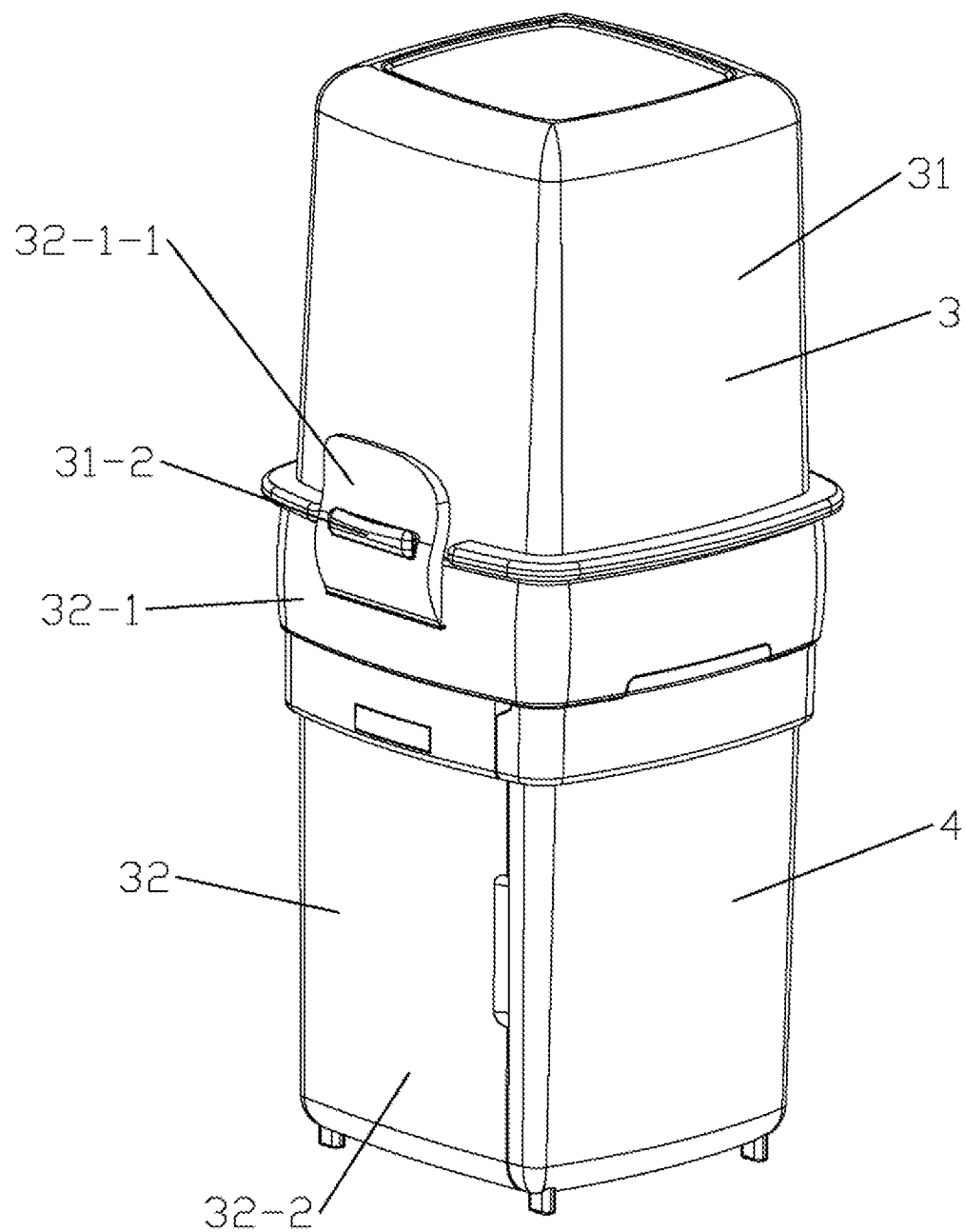
FIG. 16 is a schematic structural view of an oral cleaning kit of the present disclosure with a drawer-type holder.
Figures 1, 16:
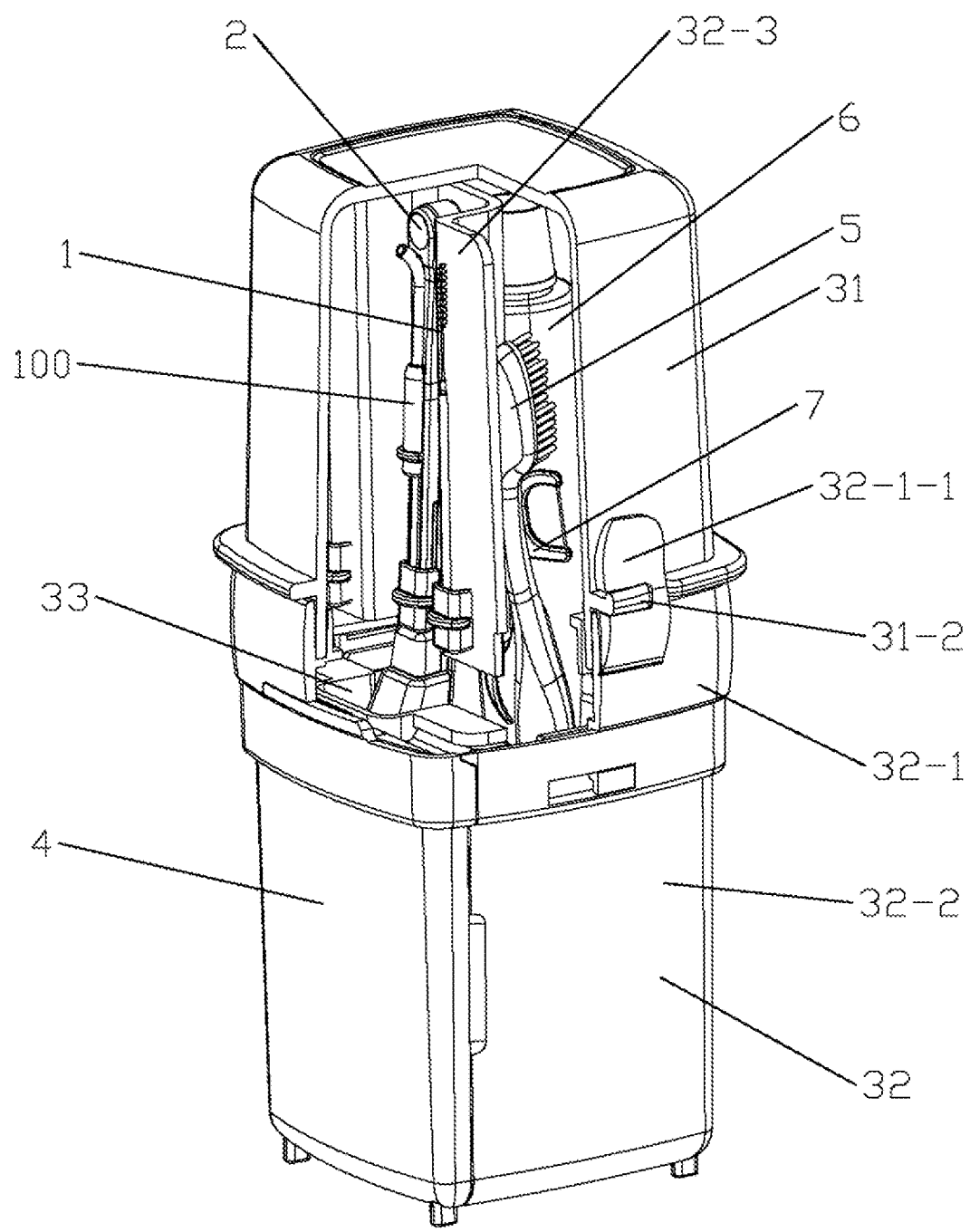
Figures 2, 16:
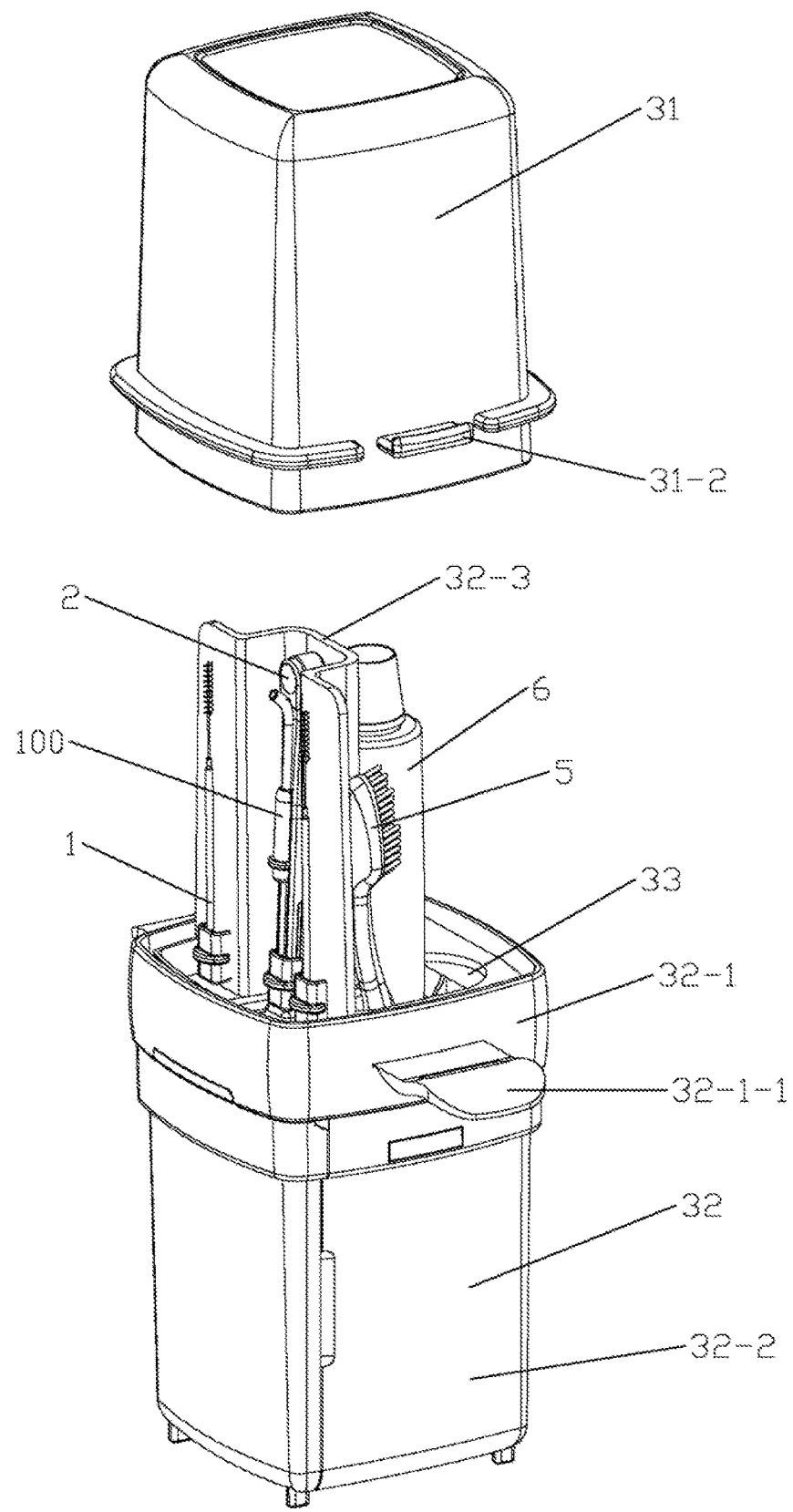
Figures 3, 16:
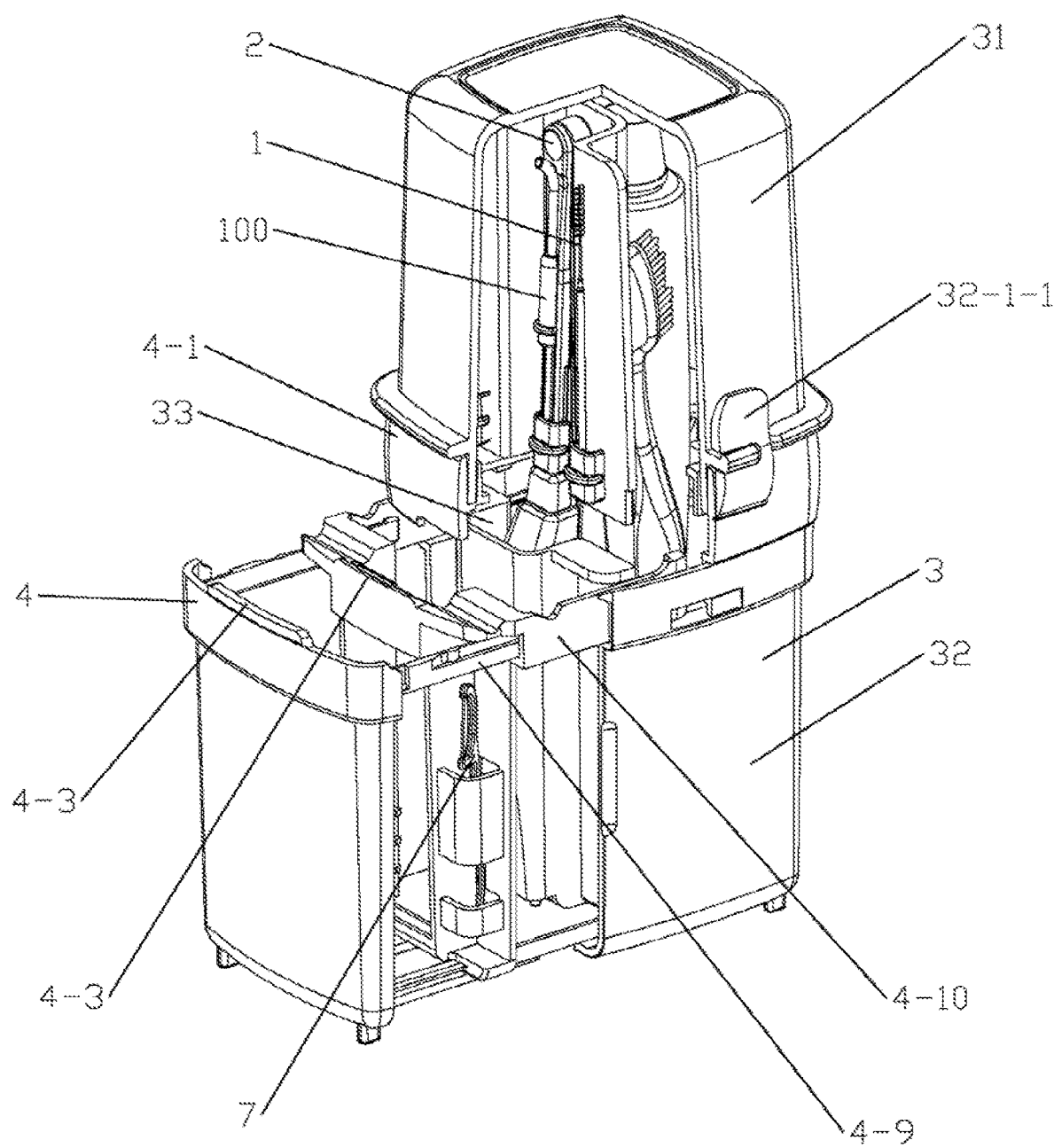
Figures 4, 16:
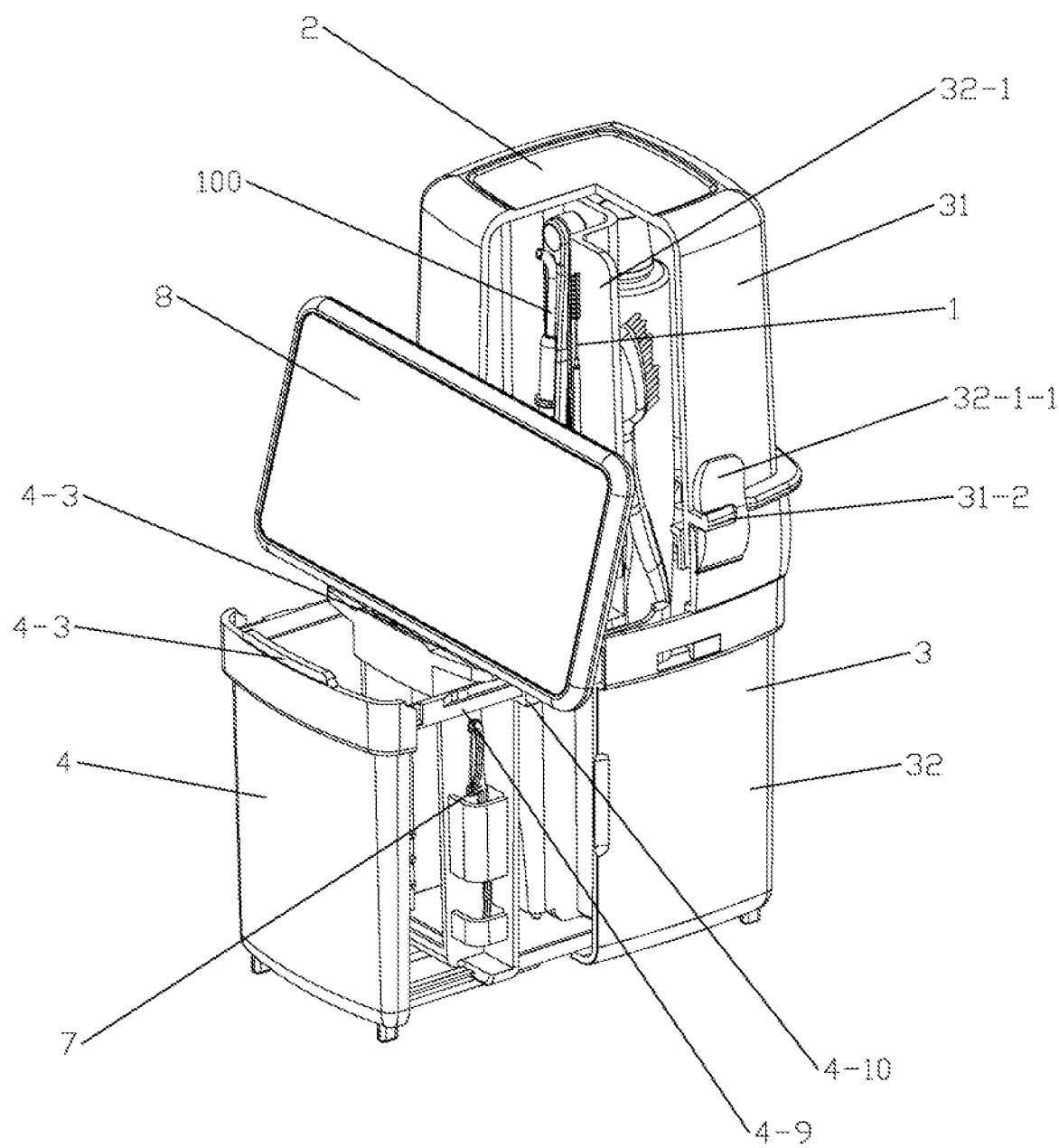

Referring to FIG. 16-3 and FIG. 16-4, the drawer-type holder 4 is a sliding drawer-type holder. The drawer-type holder 4 further includes a sliding rail 4-9 and a sliding chute 4-10. The sliding rail 4-9 is movable in the sliding chute 4-10. When the drawer-type holder 4 is pulled out, the sliding rail 4-9 protrudes out along the sliding chute 4-10, resulting in that the positioning convex steps 4-3 for positioning the mobile phone 8 are sequentially unfolded. The upper part of the base 32 is equivalent to the support plate 4-1 of the holder 4 and constitutes a positioning space for accommodating the mobile phone 8 together with the positioning convex steps 4-3. When the mobile phone 8 is taken away and the housing 4-2 of the holder 4 is pushed inward, the sliding rail 4-9 is retracted into the sliding chute 4-10, and the positioning convex steps 4-3 are sequentially folded and are also folded in the base 32 along with the holder 4.

In the present embodiment, because the drawer-type holder 4 is directly provided on the base 32, the base 32 is used to provide support for the mobile phone 8, which is convenient to use. Meanwhile, small cleaning products such as dental floss and cotton swabs may also be disposed in the storage tank 32-2 of the base 32, thereby achieving more complete functions, referring to FIG. 16-3 and FIG. 16-4. In the present embodiment, because the size of the container 3 is larger, requirements of home use may be better met.

In addition, the drawer-type holder 4 may also be unfolded or folded from the base 32 in a turning manner. When the drawer-type holder 4 is turned outward, the drawer-type holder 4 is unfolded, and the mobile phone 8 may be disposed on the drawer-type holder 4. The mobile phone 8 is taken down, the drawer-type holder 4 may be turned inward, and the drawer-type holder 4 is folded into the base 32, which will not be described here.

Embodiment 4: An Oral Cleaning Kit of the Present Disclosure with a Flip-Type Holder Referring to FIG. 19 to FIG. 24, the difference between the present embodiment and Embodiment 2 lies in that: in the present embodiment, the holder 4 is a flip-type holder.

The oral cleaning kit of the present disclosure includes an internal interdental brush 100, an oral viewer 2, a container 3, a holder 4, a toothbrush 5, toothpaste 6, and dental floss 7.

The internal interdental brush 100 is mounted on the oral viewer 2 through a connection mechanism 300. The toothbrush 5 is an electric toothbrush 5, the electric toothbrush 5 including a toothbrush head 5-1 and a host 5-2. In the present embodiment, the dental floss 7 includes a connection mechanism 7-1 and a working portion 7-2, the working portion 7-2 of the dental floss being mounted on the oral viewer 2 through the connection mechanism 7-1, referring to FIG. 19-3. In the present embodiment, the oral viewer 2, the host 5-2 of the toothbrush 5, the toothpaste 6, the internal interdental brush 100, etc. may be disposed in the front storage space 33-1. The dental floss 7, the toothbrush head 5-1, the internal interdental brush 100, etc. may be disposed in the rear storage space 33-2.

Figure 19:
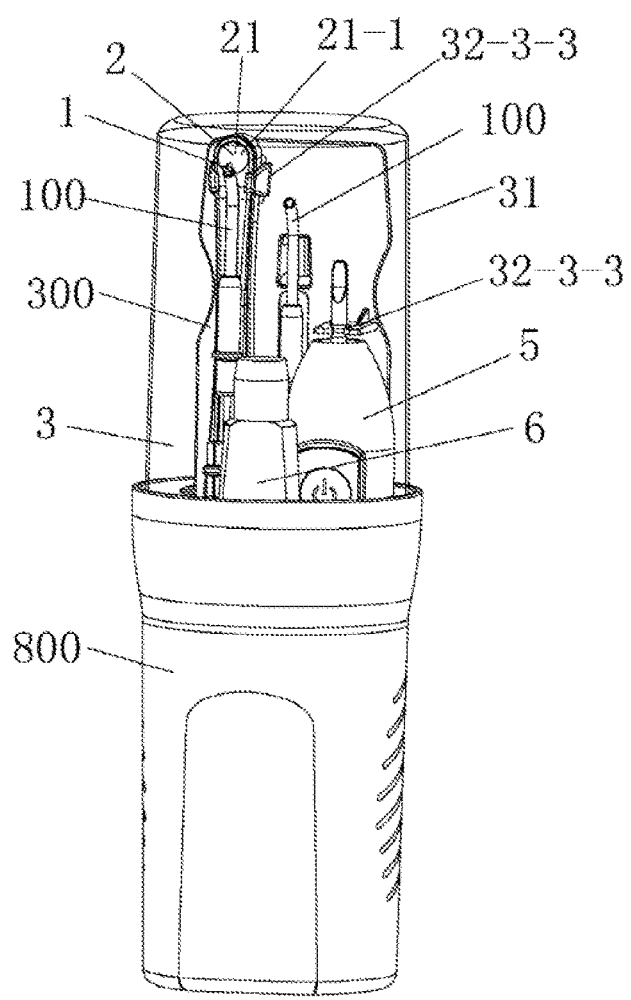
FIG. 19 is a schematic structural view of an oral cleaning kit of the present disclosure with a flip-type holder.
Figure 1:
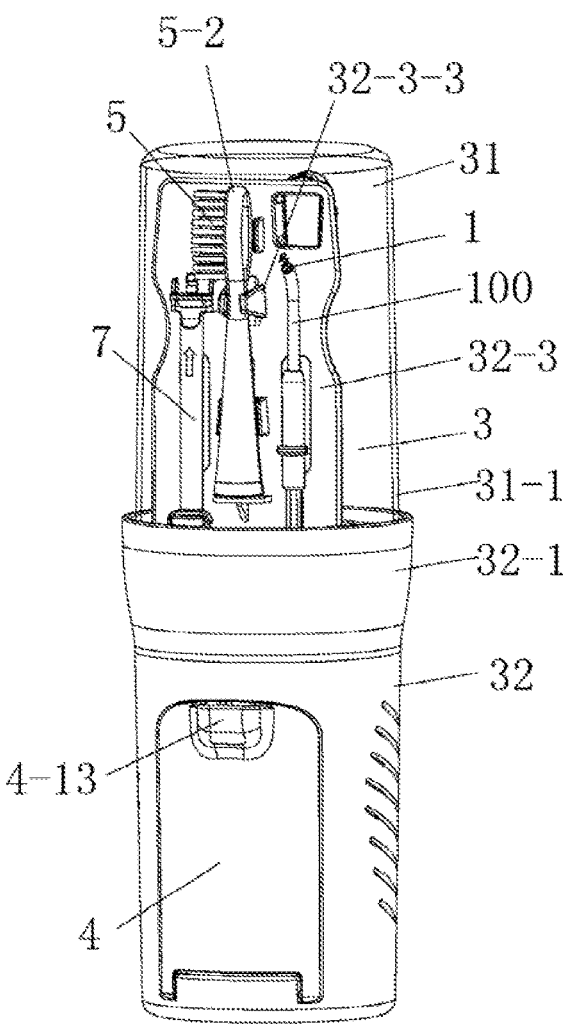
Figures 2, 19:
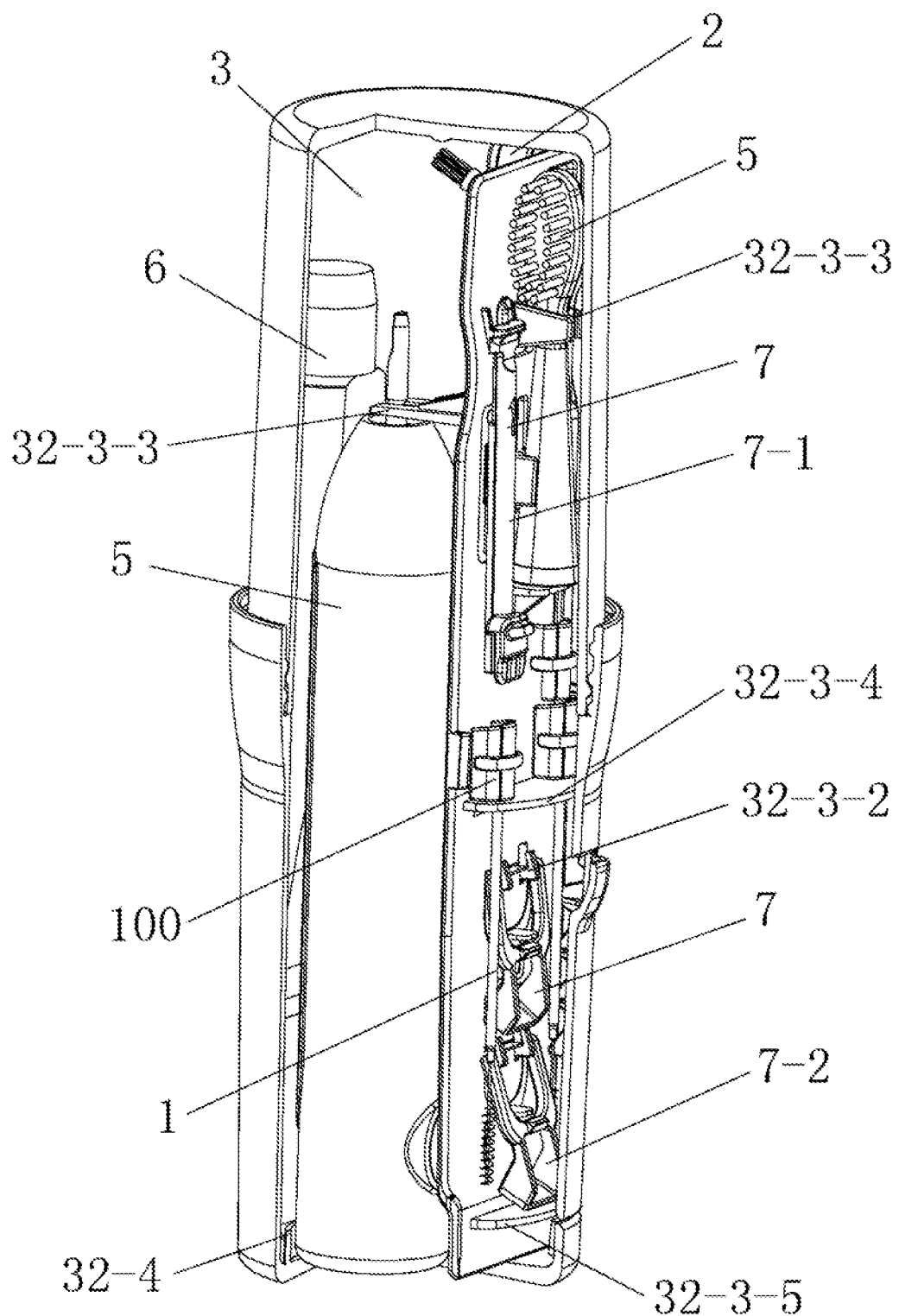
Figures 3, 19:
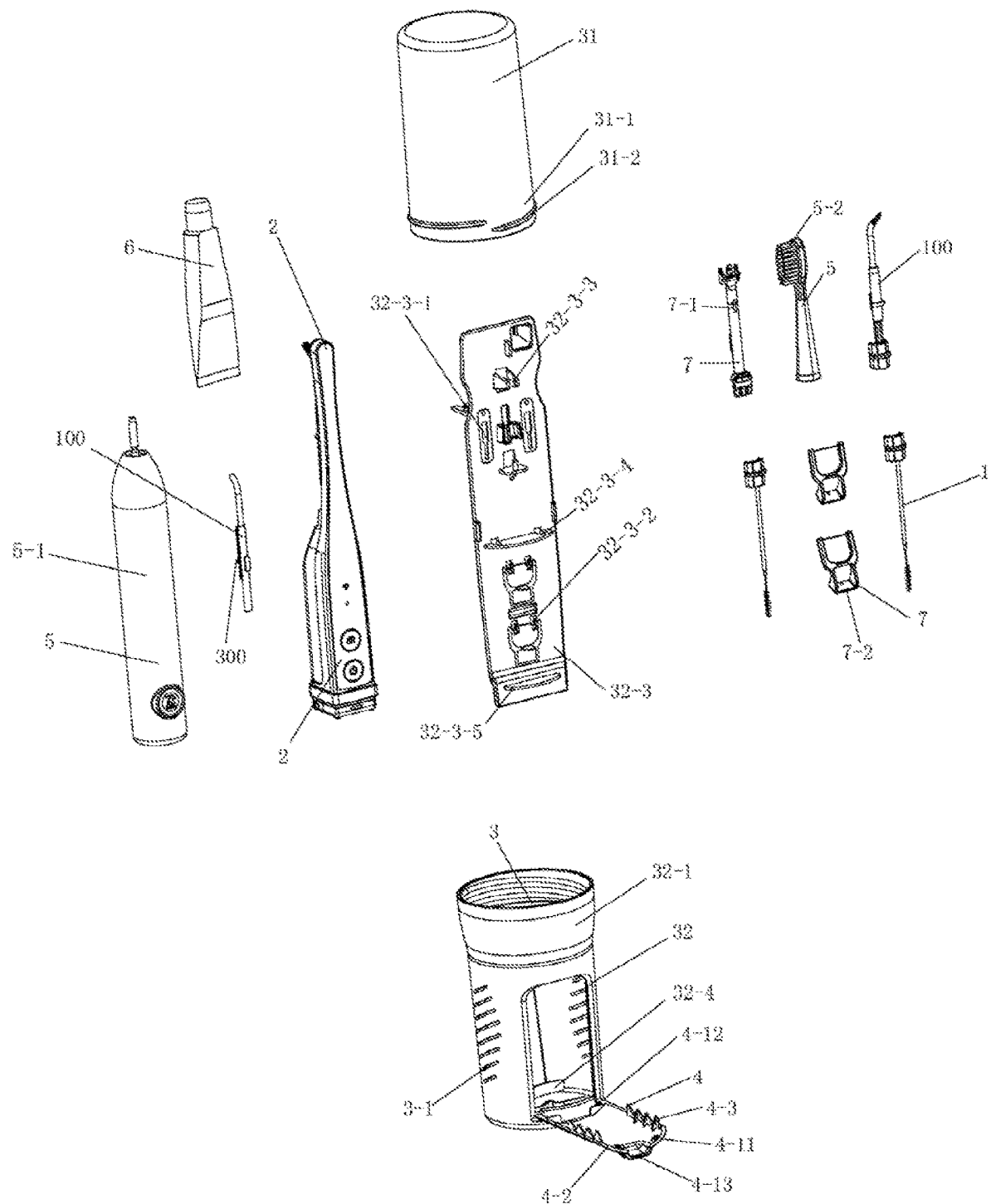
Figure 20:
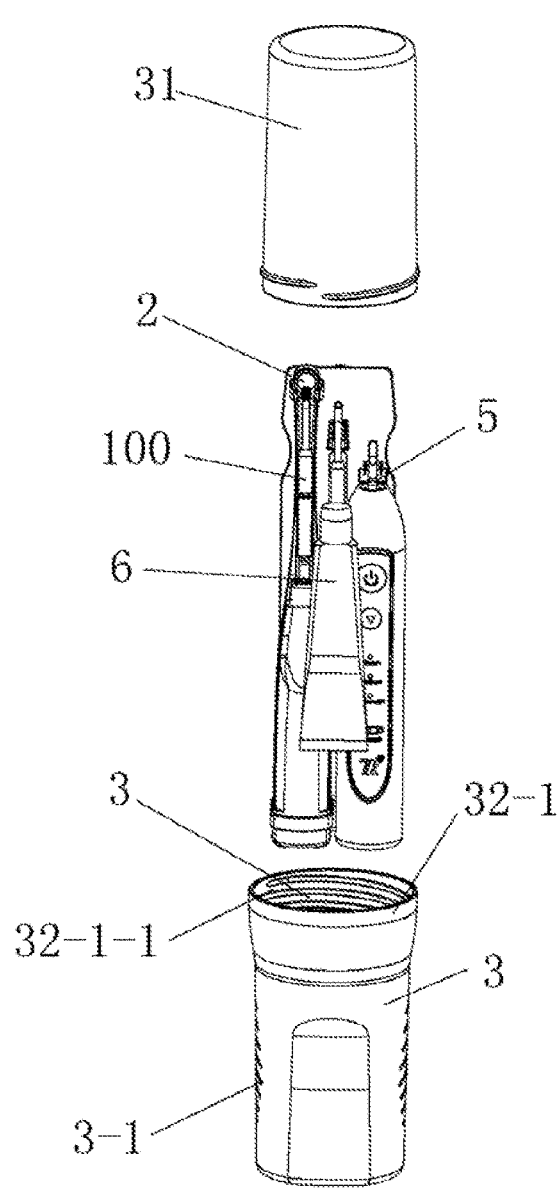
FIG. 20 is a schematic assembly view of FIG. 19.
Figure 1:
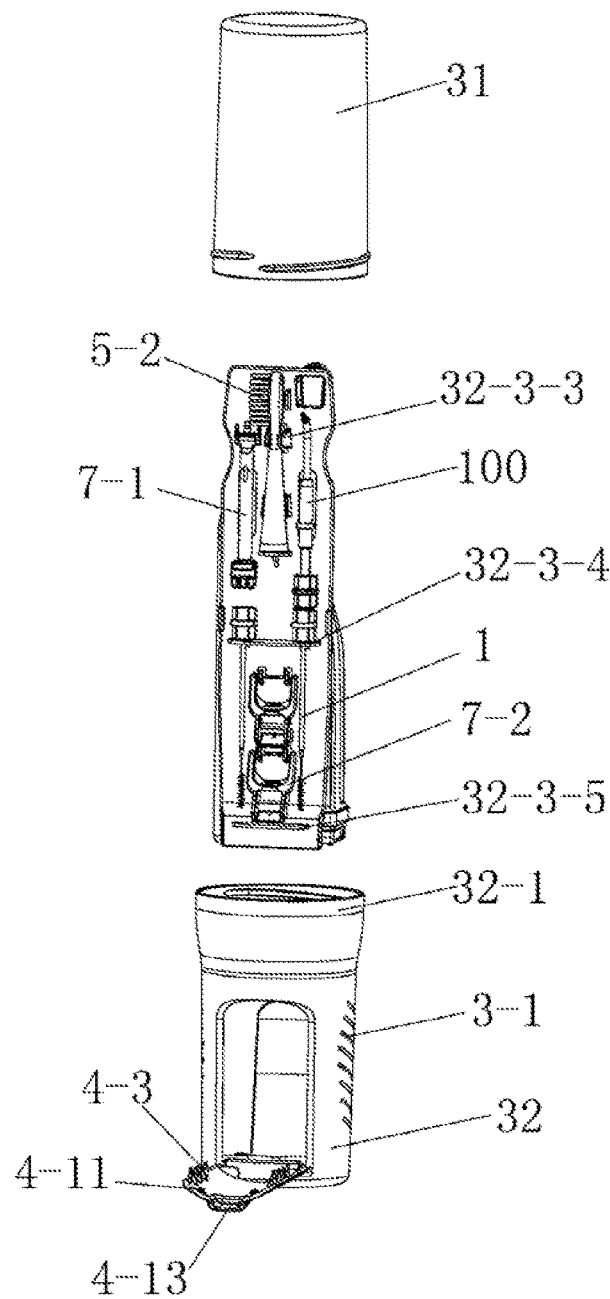
Figure 21:
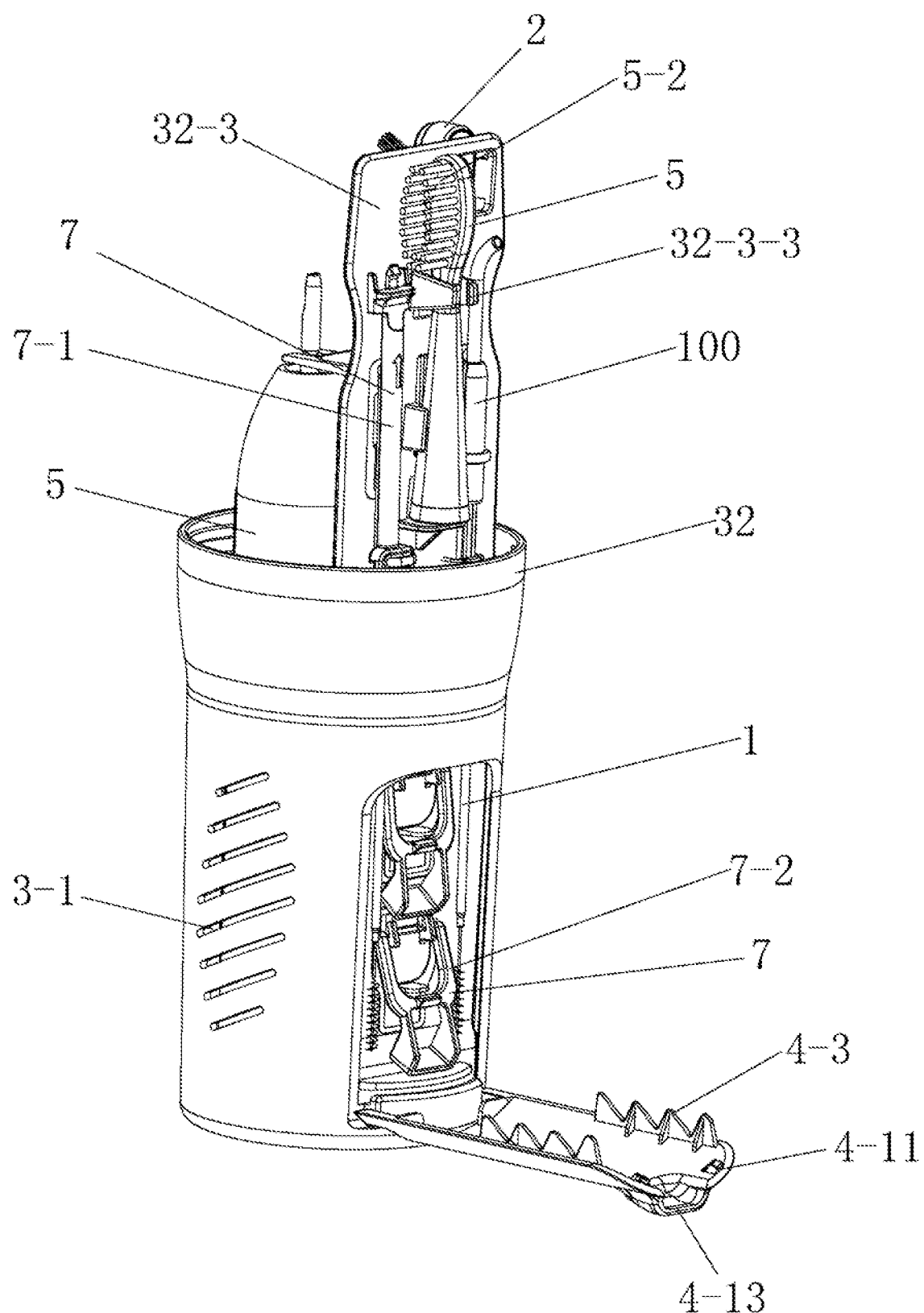
FIG. 21 is a schematic structural view of an unfolded flip-type holder.
Figure 22:
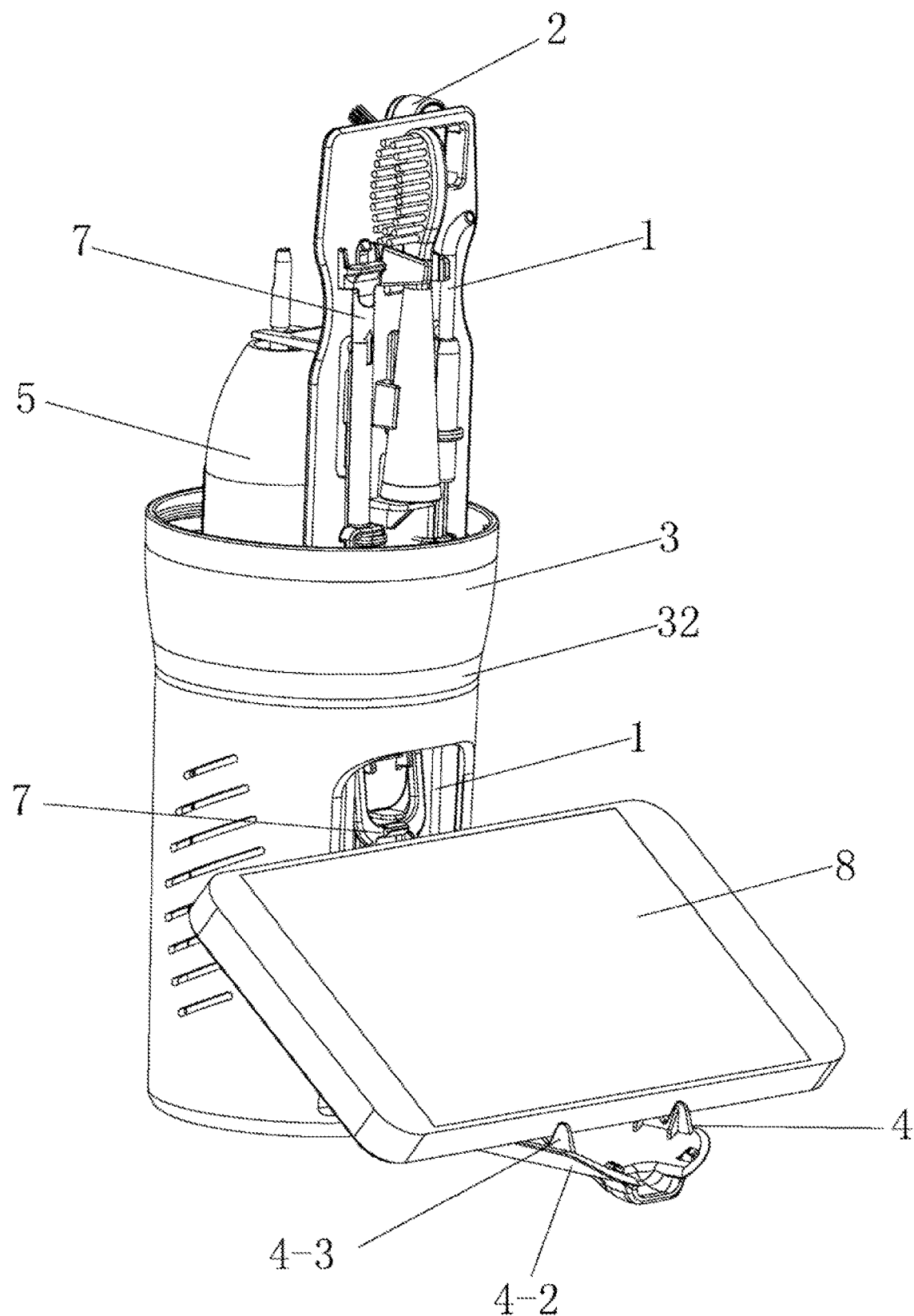
FIG. 22 is a schematic structural view of a mobile phone disposed on a flip-type holder.
Figure 23:
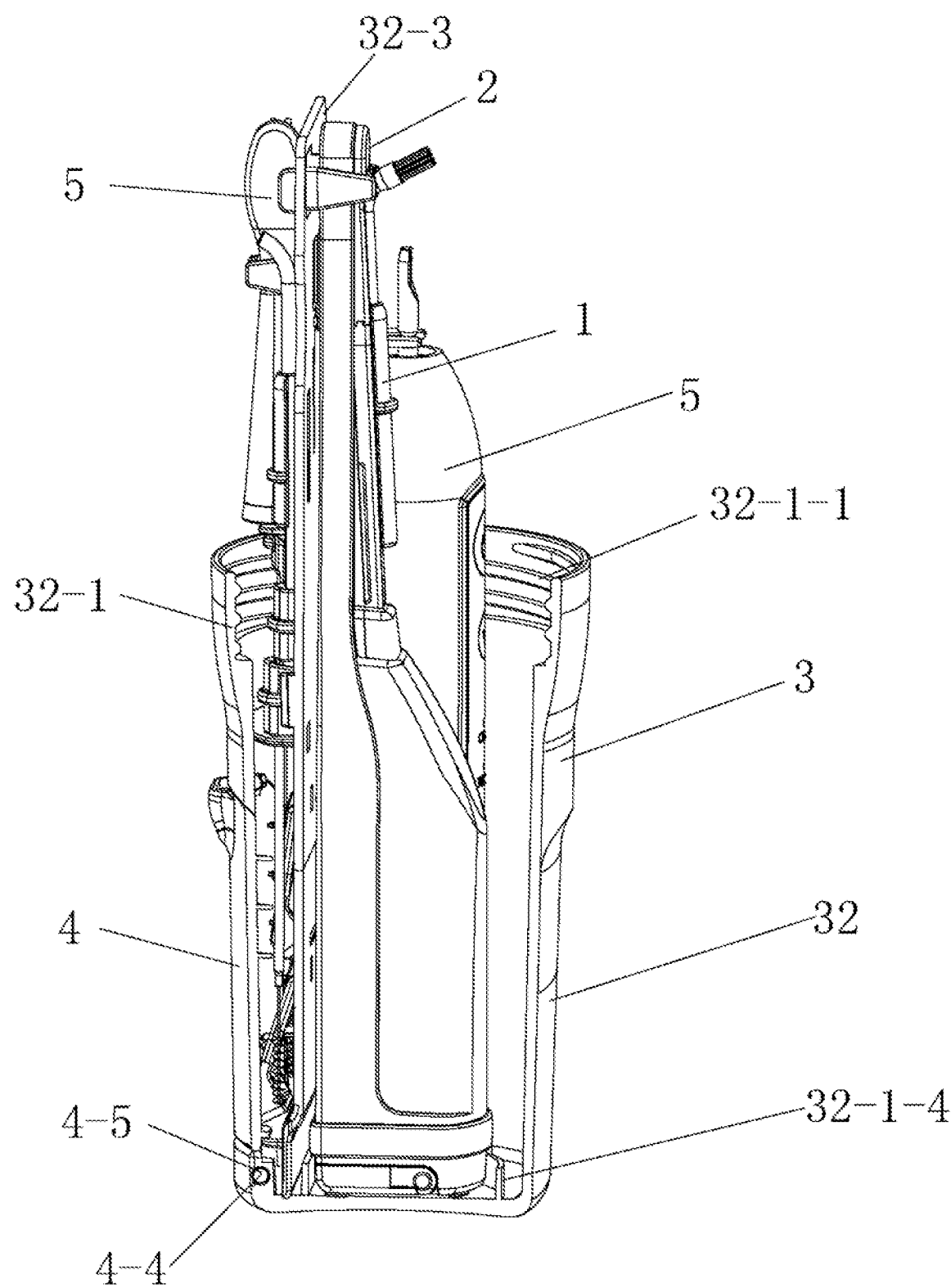
FIG. 23 is a sectional view of a folded flip-type holder.
Figure 24:
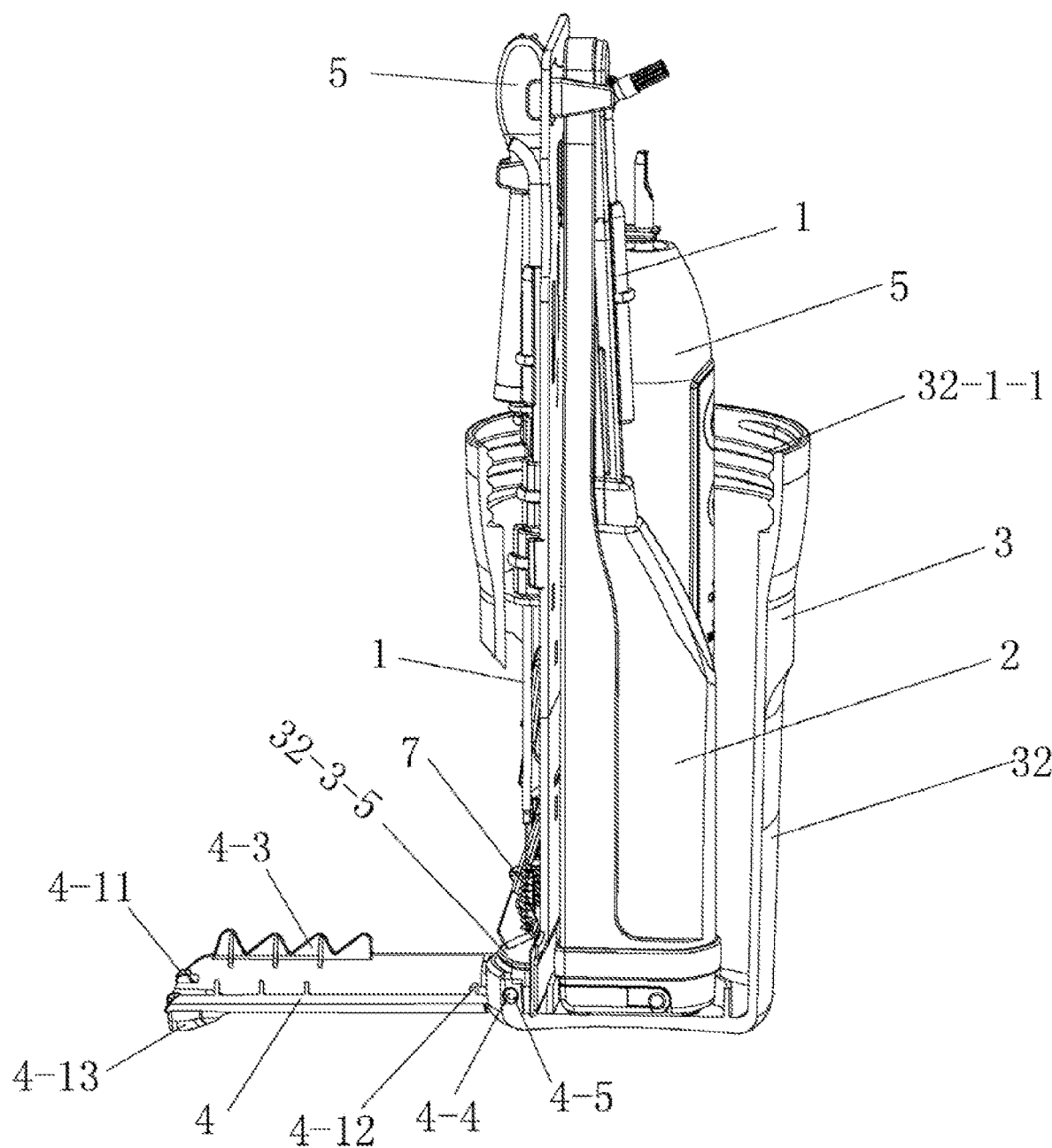
FIG. 24 is a sectional view of an unfolded flip-type holder.

Referring to FIG. 19 to FIG. 20-1, in the present embodiment, the base 32 includes a fixed clamping ring 32-1, a storage tank 32-2 and a partition plate 32-3. A positioning slot 32-4 for fixing the oral viewer 2 and the host 5-2 is also provided at the bottom of the base 32. The partition plate 32-3 faces one side of the holder 4 and the rear storage space 33-2. The upper part is provided with a positioning clamping slot 32-3-3 for fixing the toothbrush head 5-1 and a positioning slot 32-3-1 capable of embedding the connection mechanism 7-1 of the dental floss 7 and the internal interdental brush 100. The middle is provided with a baffle plate 32-3-4, a positioning slot 32-3-1 capable of suspending the interdental brush 1 being provided on the baffle plate 32-3-4. The lower part is provided with a positioning hook 32-3-2 capable of suspending the working portion 7-2 of the dental floss 7. The bottom is provided with a limiting convex step 32-3-5, the limiting convex step 32-3-5 can cooperate with a limiting plate 4-12 on the holder 4, and when the holder 4 is folded, the limiting plate 4-12 is located at the upper side of the limiting convex step 32-3-5, and the partition plate 32-3 cannot be disengaged from the base 32. The partition plate 32-3 faces one side of the front storage space 33-1, and is provided with a positioning clamping slot 32-3-3 capable of fixing the oral viewer 2 and the host 5-2 of the electric toothbrush 5 and a positioning slot 32-3-1 capable of embedding the internal interdental brush 100. The positioning clamping slot 32-3-3 and the positioning slot 32-4 at the bottom of the base 32 cooperate to fix the oral viewer 2 and the host 5-2 to the base 32. The base 32 is provided with a vent 3-1. The provision of the vent 3-1 may ensure the evaporation of residual water in the container 3, keep the dryness of the storage space 33 of the container 3, effectively prevent the growth of bacteria, and avoid the residual water from causing short circuit, aging and accidental damage of electronic components, thereby making the oral cleaning kit 800 safer and more hygienic.

In the present embodiment, the holder 4 is a flip-type holder 4 that is provided on the base 32 of the container 3. In the present embodiment, the flip-type holder 4 is an opening-closing flip-type holder, the flip-type holder 4 including a housing 4-2, a positioning convex step 4-3, a rotation shaft 4-4, a rotation shaft mounting slot 4-5, and a switch buckle position 4-11. After the holder 4 and the base 32 are disconnected by pressing down the switch buckle position 4-11, the holder 4 is rotated around the rotation shaft 4-4, the housing 4-2 may be opened, and the upper part of the base 32 is equivalent to the support plate 4-1 of the holder 4 and constitutes a positioning space for accommodating the mobile phone 8 together with the positioning convex step 4-3. When the mobile phone 8 is taken away, the housing 4-2 is rotated around the opposite direction of the rotation shaft 4-4, and the housing 4-2 is connected and locked to the base 32 through the buckle position 4-11 to fold the holder, referring to FIG. 21 to FIG. 24.

Because the flip-type holder 4 may be directly provided on the base 32 through the rotation shaft 4-4, the housing 4-2 is directly rotated through the rotation shaft 4-4 to unfold or fold the holder 4. The structure is simple, and the use process is also more convenient. Moreover, after the housing 4-2 is opened, the working portion 7-2 of the dental floss 7 disposed at the lower part of the storage space 33 is easily taken out and stored, and the use process is more convenient.

In the present embodiment, a waterproof step 4-13 is provided near the switch buckle position 4-11 of the holder 4. When the holder 4 is unfolded, the waterproof step 4-13 is supported on a work table surface to form a support position, which jointly forms a stable plane together with the base 32. Moreover, by designing the height of the waterproof step 4-13, the mobile phone 8 may be kept away from the wet table surface, and the use process is safer and more hygienic.

It should be noted that the structures disclosed and described herein may be replaced with other structures having the same effect, and the embodiments described herein are not the only structures that implement the present disclosure. Although the preferred embodiments of the present disclosure have been described and illustrated herein, it will be obvious to those skilled in the art that these embodiments are merely illustrative, and those skilled in the art can make numerous changes, improvements and replacements without departing from the present disclosure. Therefore, the scope of protection of the present disclosure should be defined in accordance with the spirit and scope of the claims appended hereto.

The invention claimed is:

1. An oral cleaning kit, comprising:
   a container capable of containing a first dental tool and a second dental tool, wherein:
   the container includes an upper cover, a base, a partition plate, and a storage space whose boundaries include the upper cover and the base;
   the upper cover is detachably mounted on the base;
   the partition plate is positioned parallel to a long axis of the container and partitions the storage space into a first region for holding the first dental tool and into a second region for holding the second dental tool;
   the first dental tool and the second dental tool are movably coupled along a vertical wall of the partition plate;
   the partition plate includes a positioning slot for positioning the first dental tool or the second dental tool; and
   the first dental tool and the second dental tool are mounted in the storage space toward the base; and
   a holder disposed on the container as an auxiliary structure for holding a mobile phone.

2. The oral cleaning kit according to claim 1, wherein the base includes:
   a storage tank;
   a fixed clamping ring provided at an open end of the storage tank; and
   a rib plate and a positioning slot hole, connected to the upper cover, provided on the fixed clamping ring, wherein:
   the positioning slot hole is provided on the rib plate.

3. The oral cleaning kit according to claim 2, further including an upper cover connecting mechanism at an upper end of the fixed clamping ring, wherein the upper cover connecting mechanism is selected from the group consisting of: a concave-convex engaging connection mechanism, a threaded connection mechanism, an interference fit connection mechanism, a hinge connection mechanism, and a buckle connection mechanism.

4. The oral cleaning kit according to claim 1, wherein the partition plate includes a positioning hook for fixing the first dental tool or the second dental tool.

5. The oral cleaning kit according to claim 1, wherein the container is provided with a vent on the base.

6. The oral cleaning kit according to claim 1, wherein the first dental tool is an internal interdental brush that includes:
   an interdental brush that is mounted in an elbow, the interdental brush having:
   a connecting body; and
   a working portion at a front end of the connecting body, wherein the working portion is capable of sliding inside the elbow.

7. The oral cleaning kit according to claim 6, wherein the internal interdental brush is detachably mounted on the second dental tool.

8. The oral cleaning kit according to claim 1, wherein both the first and second dental tools are capable of being mounted in the first region of the storage space.

9. The oral cleaning kit according to claim 1, wherein the upper cover of the container is a cup capable of holding liquid when tooth brushing.

10. The oral cleaning kit according to claim 1, wherein the holder is one selected from the group consisting of: a drawer-type holder, a flip-type holder, and a rotation-type holder.

11. The oral cleaning kit according to claim 10, wherein:
    the holder is the rotation-type holder and comprises a support plate, a housing, a positioning convex step, a rotation shaft, a rotation shaft mounting slot, and a holder mounting slot;
    the support plate is provided on the housing and is mounted in the rotation shaft mounting slot through the rotation shaft such that the mobile phone can be mounted in a space between the positioning convex step and the support plate, the positioning convex step can prevent the mobile phone from sliding, and the support plate provides support for the mobile phone; and
    the holder mounting slot can mount the holder on the upper cover of the container.

12. The oral cleaning kit according to claim 11, wherein the support plate has at least one angle adjustment position.

13. The oral cleaning kit according to claim 11, wherein an angle β between the support plate of the holder for the mobile phone and an end surface of the housing is continuously adjustable.

14. The oral cleaning kit according to claim 11, wherein a groove for facilitating the opening of the support plate is provided on the housing of the holder.

15. The oral cleaning kit according to claim 11, wherein an inner surface of the support plate of the holder comprises a mirror.

16. The oral cleaning kit according to claim 10, wherein the holder is the drawer-type holder that can be folded by pushing in and unfolded by pulling out.

17. The oral cleaning kit according to claim 16, wherein the drawer-type holder is disposed on the base of the container.

18. The oral cleaning kit according to claim 17, wherein the drawer-type holder is a sliding drawer-type holder; the drawer-type holder further comprises a sliding rail and a sliding chute; the sliding rail is movable in the sliding chute; when the drawer-type holder is pulled out, the sliding rail protrudes out along the sliding chute, resulting in positioning convex steps for mobile phone positioning to be sequentially unfolded; an upper part of the base is equivalent to the support plate of the holder and constitutes a positioning space for accommodating the mobile phone together with the positioning convex steps; and when the mobile phone is taken away and the housing is pushed inward, the sliding rail is retracted into the sliding chute, and the positioning convex steps are sequentially folded and are also folded in the base along with the holder.

19. The oral cleaning kit according to claim 10, wherein the holder is the flip-type holder that is disposed on the container.

* * * * *